(12) United States Patent
Civelli et al.

(10) Patent No.: US 6,790,608 B2
(45) Date of Patent: Sep. 14, 2004

(54) METHODS OF IDENTIFYING AND ADP-GLUCOSE RECEPTOR LIGAND, AGONIST OR ANTAGONIST

(75) Inventors: Olivier Civelli, Irvine, CA (US); Hans-Peter Nothacker, Irvine, CA (US); Zhiwei Wang, Irvine, CA (US); Rainer Reinscheid, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/780,576

(22) Filed: Feb. 9, 2001

(65) Prior Publication Data

US 2002/0072072 A1 Jun. 13, 2002

Related U.S. Application Data

(60) Provisional application No. 60/234,025, filed on Sep. 20, 2000.

(51) Int. Cl.[7] .......................... C12Q 1/00; G01N 33/53; C07K 14/00
(52) U.S. Cl. .............................. 435/4; 435/7.1; 530/350
(58) Field of Search ........................ 435/4, 7.1; 436/66; 530/350

(56) References Cited

U.S. PATENT DOCUMENTS

| 6,060,272 A | * | 5/2000 | Li et al. ..................... 435/69.1 |
| 2001/0046497 A1 | * | 11/2001 | Zhang et al. ............ 424/143.1 |
| 2002/0156246 A1 | * | 10/2002 | Glucksmann et al. .. 530/388.26 |
| 2003/0170777 A1 | * | 9/2003 | Conley et al. ............. 435/69.1 |

FOREIGN PATENT DOCUMENTS

| WO | WO 98/50549 | 11/1998 | ........... C12N/15/12 |
| WO | WO 99/57245 | 11/1999 | |
| WO | WO 00/28028 | 5/2000 | |
| WO | WO 00/31258 | 6/2000 | |
| WO | WO 01/46454 | 6/2001 | |

OTHER PUBLICATIONS

Nomura et al, Swiss–Prot, Accession No. Q15391, Huly 15, 1998.*
Brass, S., "Cardiovascular Biology: Small Cells, Big Issues," *Nature* 409:145–147 (2001).
Chambers et al., "A G Protein–coupled Receptor for UDP-–Glucose," *J. Biol. Chem.* 275:10767–10771 (2000).
Hollopeter et al., "Identification of the Platelet ADP receptor targeted by Antithrombotic Drugs," *Nature* 409:202–207 (2001).
Zhang et al., "ADP is the Cognate Ligand for the Orphan G Protein–coupled Receptor SP1999," *J. Biol. Chem.* 276:8608–8615 (2001), published, JBC Papers in Press, Dec. 4, 2000, DOI 10.1074/jbc.M009718200 (2000).
GENBANK Accession No. AA274112 (Mar. 28, 1997).
GENBANK Accession No. AA447306 (Apr. 5, 1998).
GENBANK Accession No. AC024886 (Feb. 17, 2001).
GENBANK Accession No. AI829607 (Dec. 19, 1999).
GENBANK Accession No. AW045980 (Sep. 18, 1999).
GENBANK Accession No. AW976204 (Jun. 2, 2000).
GENBANK Accession No. D81412 (Feb. 9, 1996).
GENBANK Accession No. D13626 (Feb. 3, 1999).

* cited by examiner

*Primary Examiner*—Gary Kunz
*Assistant Examiner*—Ruixiang Li
(74) *Attorney, Agent, or Firm*—McDermott Will & Emery LLP

(57) ABSTRACT

The present invention provides an isolated nucleic acid molecule containing a nucleotide sequence which encodes an ADP-glucose receptor, and isolated polynucleotides therefrom. Also provided is an isolated ADP-glucose receptor polypeptide, an isolated immunogenic peptide therefrom, and antibodies specific therefor. The invention also provides a method of identifying an ADP-glucose receptor agonist or antagonist, by contacting an ADP-glucose receptor with one or more candidate compounds under conditions suitable for detection of a G-protein coupled signal in response to ADP-glucose, and identifying a candidate compound that alters production of the signal. Further provided is a method of identifying an ADP-glucose receptor ligand, by contacting an ADP-glucose receptor with one or more candidate compounds under conditions suitable for detecting selective binding of ADP-glucose to ADP-glucose receptor, and identifying a candidate compound that selectively binds the ADP-glucose receptor. Also provided are methods of diagnosing or determining susceptibility to ADP-glucose receptor associated conditions, by detecting in a sample from the individual expression of ADP glucose receptor nucleic acid molecules or polypeptides.

20 Claims, 6 Drawing Sheets

Figure 1

METHODS OF IDENTIFYING AND ADP-GLUCOSE RECEPTOR LIGAND, AGONIST OR ANTAGONIST

This application claims the benefit of U.S. Provisional Application No. 60/234,025, filed Sep. 20, 2000, and is incorporated herein by reference.

BACKGROUND OF THE INVENTION

The present invention relates generally to the field of G-protein coupled receptors and, more specifically, to therapeutic and diagnostic compositions and methods relating to ADP-glucose receptor.

G-protein coupled receptors (GPCRs) comprise a large and growing family of integral membrane proteins which transduce extracellular signals into cellular responses. The natural agonists of different GPCRs range from peptide and non-peptide neurotransmitters, hormones and growth factors, to lipids, nucleoside-sugars, amino acids, light and odorants.

G-protein coupled receptors are involved in a variety of critical biological functions, and have proven to be important pharmacological targets. It is estimated that over 50% of current drugs are targeted towards GPCRs, and represent about a quarter of the 100 top-selling drugs worldwide. G-protein coupled receptors are also linked to a large number of hereditary diseases.

Thus, there exists a need to identify novel G-protein coupled receptors and their ligands, to identify the physiological function of such receptors, and to develop methods of screening for therapeutic compounds that specifically target these receptors. There also exists a need to identify individuals having or at risk of developing diseases associated with aberrant function or expression of G-protein coupled receptors. The present invention satisfies these needs and provides related advantages as well.

SUMMARY OF THE INVENTION

The present invention provides an isolated nucleic acid molecule containing a nucleotide sequence which encodes an ADP-glucose receptor. Further provided are vectors and cells containing the isolated nucleic acid molecule. The invention also provides an isolated polynucleotide, containing at least 20 contiguous nucleotides from the nucleotide sequence designated SEQ ID NO:1 or from the complement thereof.

Also provided is an isolated ADP-glucose receptor polypeptide. Further provided is an isolated immunogenic peptide, containing at least 10 contiguous residues of the amino acid sequence designated SEQ ID NO:2. The invention also provides an antibody specific for the isolated ADP-glucose receptor polypeptide, and an antibody specific for the isolated immunogenic peptide.

The invention also provides a method of identifying an ADP-glucose receptor agonist or antagonist. The method is practiced by contacting an ADP-glucose receptor with one or more candidate compounds under conditions suitable for detection of a G-protein coupled signal in response to ADP-glucose, and identifying a candidate compound that alters production of the signal. Such a compound is characterized as an ADP-glucose receptor agonist or antagonist.

Also provided is a method of identifying an ADP-glucose receptor ligand. The method is practiced by contacting an ADP-glucose receptor with one or more candidate compounds under conditions suitable for detecting selective binding of ADP-glucose to ADP-glucose receptor, and identifying a candidate compound that selectively binds the ADP-glucose receptor. Such a compounds is characterized as an ADP-glucose receptor ligand.

Further provided are methods of diagnosing or determining susceptibility to ADP-glucose receptor associated conditions. In one embodiment, the method is practiced by detecting in a sample from the individual expression of a nucleic acid molecule which specifically hybridizes to the complement of SEQ ID NO:1. Abnormal expression of the nucleic acid indicates that the individual has or is susceptible to an ADP-glucose receptor associated condition. In an alternative embodiment, the method is practiced by detecting in a sample from the individual expression of a polypeptide which specifically binds an ADP-glucose receptor ligand. Abnormal expression of the polypeptide indicates that the individual has or is susceptible to an ADP-glucose receptor associated condition.

BRIEF DESCRIPTION OF THE DRAWINGS

FIG. 1 shows the nucleotide sequence (SEQ ID NO:1) and deduced amino acid sequence (SEQ ID NO:2) of the human ADP-glucose receptor. The seven predicted transmembrane domains are underlined.

FIG. 2A shows changes in intracellular calcium concentration in CHO cells transiently transfected with $G\alpha16$ and $G\alpha qi3$ in response to ADP-glucose (filled squares), ADP-ribose (open circles), or ADP-mannose (open triangles) and in untransfected CHO cells in response to ADP-glucose (closed triangles).

FIG. 2B shows changes in intracellular calcium concentration in untransfected HEK 293 cells in response to ADP-glucose (filled squares), ADP-ribose (open circles) or ADP-mannose (open triangles). Values are mean±S.E.M. (n=3) from a representative experiment.

DETAILED DESCRIPTION OF THE INVENTION

Figure 2:
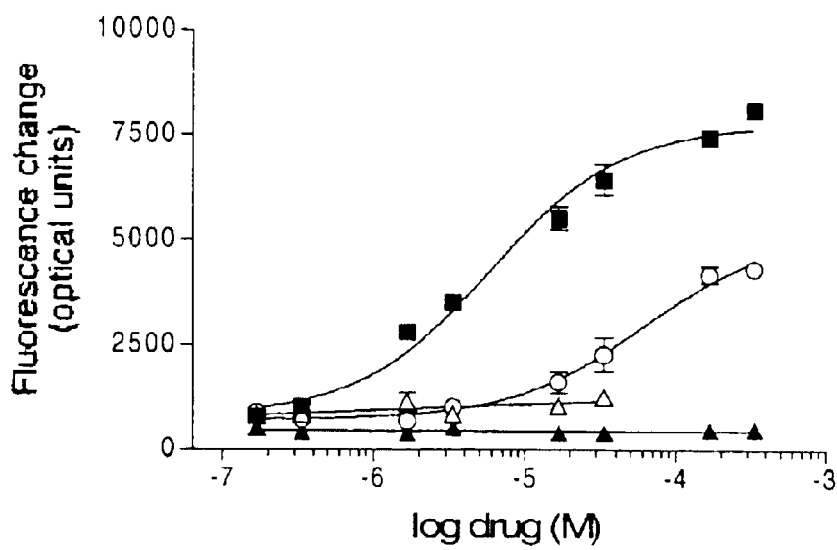
FIG. 2 shows signaling through ADP-glucose receptor as a function of drug concentration.
Figure 2:
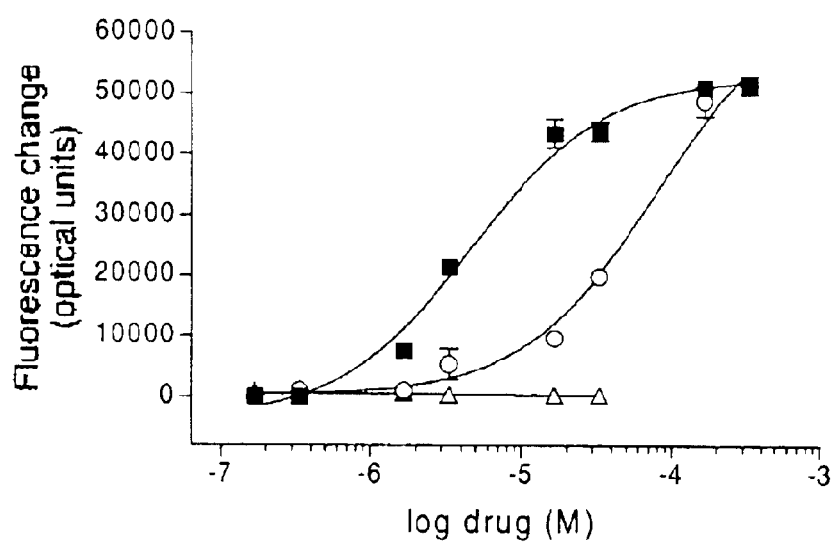

The invention relates to the identification of ADP-glucose and ADP-ribose as signal transmitters in mammals. The invention further relates to the identification of an ADP-glucose receptor and characterization of its signal transduction pathway and physiological activity. Thus, compositions and methods useful for identifying ligands, agonists and antagonists of ADP-glucose receptor are provided. Such compounds can be used therapeutically to prevent or ameliorate conditions associated with altered ADP-glucose receptor function, including conditions associated with smooth muscle contractility and vascular tone. Also provided are compositions and methods useful for diagnosing or predicting susceptibility to conditions associated with altered ADP-glucose receptor function. Such knowledge allows optimal medical care for an affected individuals, including appropriate genetic counseling and prophylactic and therapeutic intervention.

As used herein, the term "ADP-glucose receptor" refers to a polypeptide containing the amino acid sequence designated SEQ ID NO:2, or to a polypeptide containing minor modifications to the sequence designated SEQ ID NO:2, which transduces a G-protein coupled signal in response to ADP-glucose (adenosine 5'-diphosphoglucose).

Figure 1:
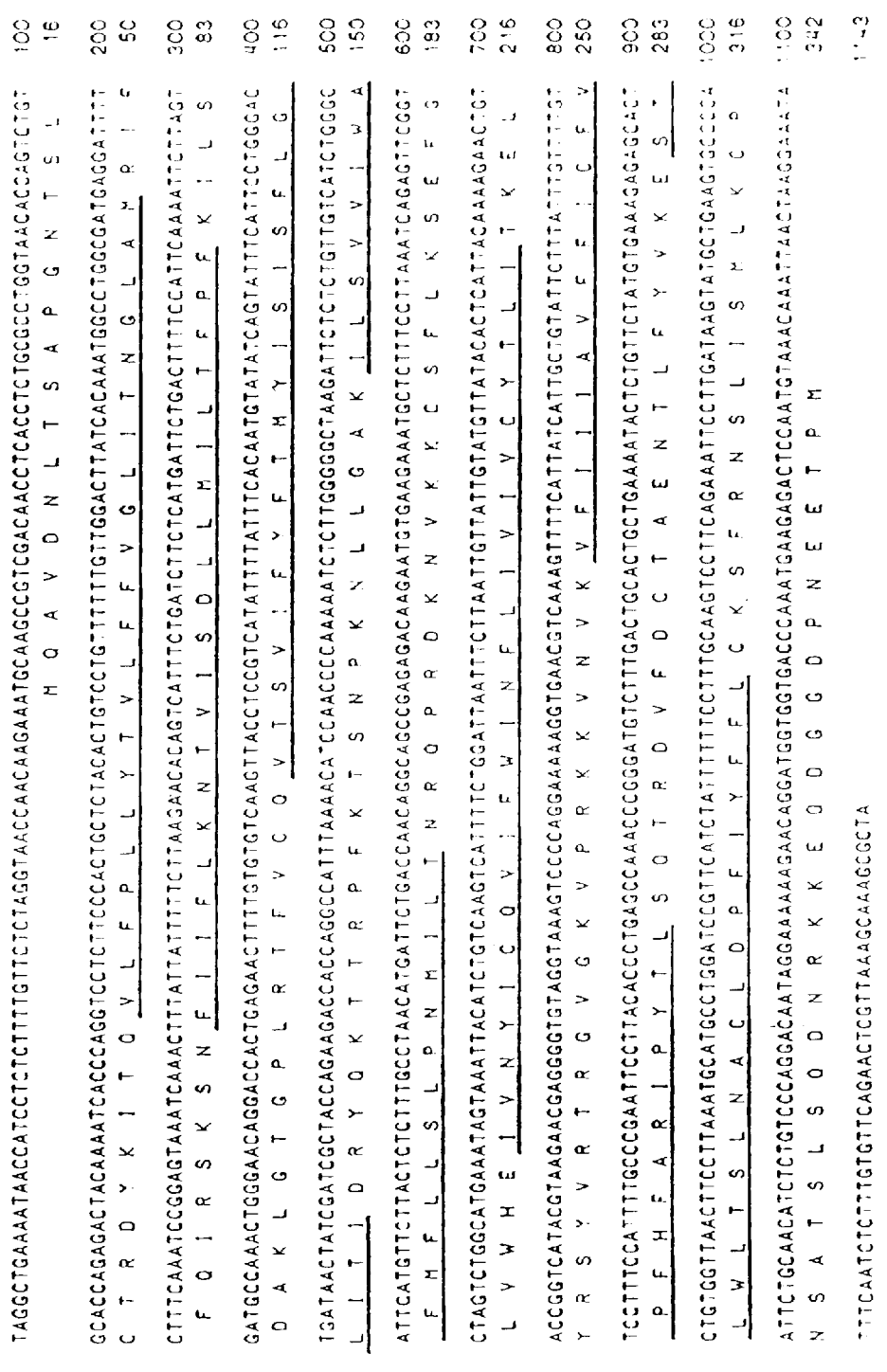

The ADP-glucose receptor polypeptide containing the amino acid sequence designated SEQ ID NO:2 is a ubiquitously expressed human seven-transmembrane-domain polypeptide that transduces G-protein coupled signals in response to ADP-glucose. The seven predicted transmembrane spanning sequences are underlined in FIG. 1.

As used herein, the term "transduces a G-protein coupled signal" refers to the ability of the receptor to transduce a G-protein coupled signal in response to ADP-glucose with an $EC_{50}$ of less than about $10^{-4}$ M, preferably less than $5\times10^{-5}$ M, more preferably less than $10^{-5}$ M, including less than $5\times10^{-6}$ M or less than $10^{-6}$ M, when transiently expressed in CHO cells. The term "$EC_{50}$" refers to the concentration of agonist required to generate half of the maximal signal.

An ADP-glucose receptor is also characterized by its ability to transduce a G-protein coupled signal in response to the nucleoside sugar ADP-ribose, although with an $EC_{50}$ about 10-fold higher than for ADP-glucose. An ADP-glucose receptor is further characterized in that it does not transduce a G-protein coupled signal in response to ADP-mannose, or transduces such a signal with an $EC_{50}$ at least 100-fold, such as at least 1000-fold, higher than for ADP-glucose.

As used herein, the term "G-protein" refers to a class of heterotrimeric GTP binding proteins, with subunits designated Gα, Gβ and Gγ, that couple to seven-transmembrane cell surface receptors to couple extracellular stimuli to intracellular messenger molecules. G-proteins are distinguished by their Gα subunits. The more than 20 different Gα subunits, encoded by 17 different genes, can be grouped into four major families: Gαs, Gαi, Gαq, and Gα12.

As described herein, the ADP-glucose receptor having the amino acid sequence designated SEQ ID NO:2 naturally couples to Gαq-containing G proteins, but also can couple to G proteins containing other Gα subunits, such as Gα16 and Gαi. Signaling through Gαq-containing G-proteins promotes intracellular calcium ion mobilization, which can be determined by assays described herein. Thus, an exemplary "G-protein coupled signal" for determining that a polypeptide specifically transduces a G-protein coupled signal in response to ADP-glucose is intracellular calcium ion mobilization.

The specificity of Gα subunits for cell-surface receptors is determined by the C-terminal five amino acids of the Gα. Thus, a variety of signal transduction pathways can be assayed to determine transduction of a G-protein coupled signal by an ADP-glucose receptor, by co-expressing a chimeric Gα containing the five C-terminal residues of a Gα known or predicted to couple to ADP-glucose receptor (such as Gαi, Gαq or Gα16), with the remainder of the protein corresponding to a Gα that couples to the signal transduction pathway to be assayed (e.g. Gαs, to assay increased cAMP production, or Gαq to assay intracellular $Ca^{2+}$ mobilization). Based on the known sequences of Gα subunits, nucleic acid molecules encoding chimeric Gα can be constructed and expressed by methods known in the art and described, for example, in Conklin et al., *Nature* 363:274–276 (1993), and Komatsuzaki et al., *FEBS Letters* 406:165–170 (1995).

Depending on the Gα subunit endogenously or recombinantly expressed in the assay system, G-protein coupled signals that can be determined include, but are not limited to, increased or decreased production or liberation of arachidonic acid, acetylcholine, diacylglycerol, cGMP, cAMP, inositol phosphate and ions; altered cell membrane potential; GTP hydrolysis; influx or efflux of amino acids; increased or decreased phosphorylation of intracellular proteins; and activation of transcription of an endogenous gene or promoter-reporter construct.

As used herein, the term "minor modification" to the sequence designated SEQ ID NO:2 refers to one or more additions, deletions or substitutions compared with the recited amino acid sequence; one or more chemical or enzymatic modifications to the polypeptide; or substitution of one or more L-configuration amino acids with corresponding D-configuration amino acids. Such modifications can be advantageous, for example, in enhancing the stability, expression level, signaling activity, or binding specificity of the receptor. The function of the modified polypeptide can be assayed by the methods described herein, to confirm that the modified polypeptide retains the ability to specifically transduce G-protein coupled signals in response to ADP-glucose.

Modifications to the amino acid sequence designated SEQ ID NO:2 can be randomly generated, such as by random insertions, deletions or substitutions of nucleotides in a nucleic acid molecule encoding SEQ ID NO:2. Alternatively, modifications can be directed, such as by site-directed mutagenesis of a nucleic acid molecule encoding SEQ ID NO:2.

Computer programs known in the art can provide guidance in predicting which amino acid residues can be modified without abolishing the function of the polypeptide (see, for example, Eroshkin et al., *Comput. Appl. Biosci.* 9:491–497 (1993)).

Additionally, guidance in modifying amino acid residues of SEQ ID NO:2 while retaining function can be provided by structure-function studies of other G-protein coupled receptors. For example, small ligands generally make contact with residues in several transmembrane helices and may also make contact with residues in the extracellular domain (Flower, *Biochimica et Biophysica Acta* 1422:207–234 (1999)). Accordingly, modifications of residues in the ligand binding pocket of the polypeptide having the amino acid sequence designated SEQ ID NO:2 are predicted to be less well tolerated than modifications to other parts of the receptor.

Based on studies of other G-protein coupled receptors, G-proteins generally make contact with the second intracellular loop and with the N and C segments of the third intracellular loop of the receptor (Wess, *Pharmacol. Ther.* 80:231–264 (1998)). Accordingly, modifications of residues within the effector binding regions of the polypeptide having the amino acid sequence designated SEQ ID NO:2 are predicted to be less well tolerated than modifications to other parts of the receptor.

Furthermore, guidance in modifying amino acid residues of SEQ ID NO:2 while retaining function can be provided by comparison of SEQ ID NO:2 with the sequence of its mammalian homologs, such as homologs in non-human primates, mouse, rat, rabbit, bovine, porcine, ovine, canine or feline species. It is well known in the art that evolutionarily conserved amino acid residues and domains are more likely to be important for maintaining biological activity than less well-conserved residues and domains. Thus, it would be expected that substituting a residue that is highly conserved among ADP-glucose receptors across species with a non-conserved residue may be deleterious, whereas making the same substitution at a residue which varies widely among species would likely not have a significant effect on biological activity. Methods of identifying homologs of SEQ ID NO:2 in other species are described further below.

Substitutions to the amino acid sequence designated SEQ ID NO:2 can either be conservative or non-conservative. Conservative amino acid substitutions include, but are not limited to, substitution of an apolar amino acid with another apolar amino acid (such as replacement of leucine with an isoleucine, valine, alanine, proline, tryptophan, phenylalanine or methionine); substitution of a charged amino acid with a similarly charged amino acid (such as replacement of a glutamic acid with an aspartic acid, or replacement of an arginine with a lysine or histidine); substitution of an uncharged polar amino acid with another uncharged polar amino acid (such as replacement of a serine with a glycine, threonine, tyrosine, cysteine, asparagine or glutamine); or substitution of a residue with a different functional group with a residue of similar size and shape (such as replacement of a serine with an alanine; an arginine with a methionine; or a tyrosine with a phenylalanine).

Additions to the amino acid sequence designated SEQ ID NO:2 include, but are not limited to, the addition of "tag" sequences at the N or C termini, or within extracellular or intracellular loops. Such tag sequence include, for example, epitope tags, histidine tags, glutathione-S-transferase (GST), and the like, or sorting sequences. Such additional sequences can be used, for example, to facilitate expression, purification or characterization of a recombinant ADP-glucose receptor.

In applications in which it is desired to ensure a 1:1 stoichiometry of receptor and G-protein, ADP-glucose receptor can be fused directly to a Gα subunit. Such fusion polypeptides can be produced from chimeric nucleic acid molecules that contain sequences encoding ADP-glucose receptor at the 5' end, linked directly to sequences encoding the desired Gα subunit. G-protein coupled receptor-Gα subunit fusion constructs and their applications are reviewed, for example, in Milligan, *Trends Pharmacol. Sci.* 21:24–28 (2000).

Deletions to the amino acid sequence designated SEQ ID NO:2 include, but are not limited to, deletion of residues at the extramembranal- or C-termini that are not critical for function. Deleted sequences can optionally be replaced by tag sequences or fusion sequences, as described previously.

Chemical and enzymatic modifications to the polypeptide containing the amino acid sequence designated SEQ ID NO:2 include but are not limited to the following: replacement of hydrogen by an alkyl, acyl, or amino group; esterification of a carboxyl group with a suitable alkyl or aryl moiety; alkylation of a hydroxyl group to form an ether derivative; phosphorylation or dephosphorylation of a serine, threonine or tyrosine residue; or–or O-linked glycosylation.

The invention provides an isolated nucleic acid molecule encoding an ADP-glucose receptor. The invention nucleic acid molecules are suitable for a variety of screening, therapeutic and diagnostic applications. For example, an invention nucleic acid molecule can be expressed in cells or in artificial signaling systems, and used to identify ADP-glucose receptor ligands, agonists and antagonists. An invention nucleic acid molecule can also be expressed in vivo, to restore ADP-glucose receptor function in cells with abnormally low expression of the receptor, or expressed in vivo in an antisense configuration to inhibit ADP-glucose receptor function in cells with abnormally high expression of the receptor.

Additionally, the invention nucleic acid molecules can be used as probes or primers to identify and isolate ADP-glucose receptor homologs from other species, or to identify structurally related receptors, using methods known in the art and described further below. Such probes and primers are also useful diagnostically to determine normal and abnormal expression of ADP-glucose receptor in human tissues, and thus to predict susceptibility to ADP-glucose receptor associated conditions.

As used herein, the terms "comprising," "having," "encoding," and "containing," and derivatives of these terms, are intended to be open-ended. The term "consisting" is intended to be closed-ended.

As used herein, the term "isolated nucleic acid molecule" is intended to mean that the nucleic acid molecule is altered, by the hand of man, from how it is found in its natural environment. For example, an isolated nucleic acid molecule can be a molecule operatively linked to an exogenous nucleic acid sequence. An isolated nucleic acid molecule can also be a molecule removed from some or all of its normal flanking nucleic acid sequences.

An isolated molecule can alternatively, or additionally, be a "substantially pure" molecule, in that the molecule is at least 60%, 70%, 80%, 90 or 95% free from cellular components with which it is naturally associated. An isolated nucleic acid molecule can be in any form, such as in a buffered solution, a suspension, a lyophilized powder, attached to a solid support (e.g. as a component of a DNA array), or in a cell.

As used herein, the term "nucleic acid molecule" refers to a polynucleotide of natural or synthetic origin, which can be single- or double-stranded, can correspond to genomic DNA, cDNA or RNA, and can represent either the sense or antisense strand or both.

The term "nucleic acid molecule" is intended to include nucleic acid molecules that contain one or more non-natural nucleotides, such as nucleotides having modifications to the base, the sugar, or the phosphate portion, or having one or more non-natural linkages, such as phosphothioate linkages. Such modifications can be advantageous in increasing the stability of the nucleic acid molecule, particularly when used in hybridization applications.

Furthermore, the term "nucleic acid molecule" is intended to include nucleic acid molecules modified to contain a detectable moiety, such as a radiolabel, a fluorochrome, a ferromagnetic substance, a luminescent tag or a detectable binding agent such as biotin. Nucleic acid molecules containing such moieties are useful as probes for detecting the presence or expression of an ADP-glucose receptor nucleic acid molecule.

An isolated nucleic acid molecule encoding an ADP-glucose receptor specifically excludes nucleic acid molecules having the exact sequence of human genomic fragments whose sequences are compiled in publically available databases, such as GenBank Accession No. AC024886 or other portions of human chromosome 3. In one embodiment, an isolated nucleic acid molecule encoding an ADP-glucose receptor does not contain nucleotide sequences normally present on human chromosome 3 which encode polypeptides other than ADP-glucose receptor.

An isolated nucleic acid molecule encoding an ADP-glucose receptor polypeptide can contain a nucleotide sequence having at least 70% identity to the nucleotide sequence designated SEQ ID NO:1. Preferably, such a molecule will have at least 75% identity, including at least 80%, 85%, 90%, 95%, 98%, 99% or greater identity to SEQ ID NO:1.

Alternatively, the isolated nucleic acid molecule encoding an ADP-glucose receptor polypeptide contains a nucleotide sequence which encodes a polypeptide having at least 70% identity to the amino acid sequence designated SEQ ID NO:2. Preferably, the encoded polypeptide will have at least 75% identity, including at least 80%, 85%, 90%, 95%, 98%, 99% or greater identity to SEQ ID NO:2.

The term "percent identity" with respect to a nucleic acid molecule or polypeptide of the invention is intended to refer to the number of identical nucleotide or amino acid residues between the aligned portions of two sequences, expressed as a percent of the total number of aligned residues, as determined by comparing the entire sequences using a BLAST 2.0 computer alignment and default parameters. BLAST 2.0 alignments can be performed as described by Tatusova et al., *FEMS Microbiol Lett.* 174:247–250 (1999).

In one embodiment, the isolated nucleic acid molecule encoding an ADP-glucose receptor contains, or consists of, a) the nucleotide sequence designated SEQ ID NO:1; b) the portion of the nucleotide sequence designated SEQ ID NO:1 that encodes SEQ ID NO:2; or c) a sequence that is degenerate with respect to either a) or b).

The invention further provides an isolated nucleic acid molecule encoding an ADP-glucose receptor polypeptide, wherein the nucleic acid molecule is operatively linked to a promoter of gene expression. As used herein, the term "operatively linked" is intended to mean that the nucleic acid molecule is positioned with respect to either the endogenous promoter, or a heterologous promoter, in such a manner that the promoter will direct the transcription of RNA using the nucleic acid molecule as a template.

Methods for operatively linking a nucleic acid to a heterologous promoter are well known in the art and include, for example, cloning the nucleic acid into a vector containing the desired promoter, or appending the promoter to a nucleic acid sequence using PCR. A nucleic acid molecule operatively linked to a promoter of RNA transcription can be used to express ADP-glucose receptor transcripts and polypeptides in a desired host cell or in vitro transcription-translation system.

The choice of promoter to operatively link to an invention nucleic acid molecule will depend on the intended application, and can be determined by those skilled in the art. For example, if a particular gene product may be detrimental to a particular host cell, it may be desirable to link the invention nucleic acid molecule to a regulated promoter, such that gene expression can be turned on or off. Alternatively, it may be preferred to have expression driven by either a weak or strong constitutive promoter. Exemplary promoters suitable for mammalian cell systems include, for example, the SV40 early promoter, the cytomegalovirus (CMV) promoter, the mouse mammary tumor virus (MMTV) steroid-inducible promoter, and the Moloney murine leukemia virus (MMLV) promoter.

The invention further provides a vector containing an isolated nucleic acid molecule encoding an ADP-glucose receptor. Exemplary vectors include vectors derived from a virus, such as a bacteriophage, a baculovirus or a retrovirus, and vectors derived from bacteria or a combination of bacterial sequences and sequences from other organisms, such as a cosmid or a plasmid. The vectors of the invention will generally contain elements such as an origin of replication compatible with the intended host cells; one or more selectable markers compatible with the intended host cells; and one or more multiple cloning sites. The choice of particular elements to include in a vector will depend on factors such as the intended host cells; the insert size; whether expression of the inserted sequence is desired; the desired copy number of the vector; the desired selection system, and the like. The factors involved in ensuring compatibility between a host cell and a vector for different applications are well known in the art.

In applications in which the vectors are to be used for recombinant expression of the encoded polypeptide, the isolated nucleic acid molecules will generally be operatively linked to a promoter of gene expression, as described above, which may be present in the vector or in the inserted nucleic acid molecule. An exemplary expression vector is the pCDNA3.1 vector (Invitrogen) described in the Example. For certain applications, however, promoter elements need not be present.

Also provided are cells containing an isolated nucleic acid molecule encoding an ADP-glucose receptor. The isolated nucleic acid molecule will generally be contained within a vector. The isolated nucleic acid molecule can be maintained episomally, or incorporated into the host cell genome.

The cells of the invention can be used, for example, for molecular biology applications such as expansion, subcloning or modification of the isolated nucleic acid molecule. For such applications, bacterial cells, such as laboratory strains of *E. coli*, are useful, and expression of the encoded polypeptide is not required.

The cells of the invention can also advantageously be used to express the encoded polypeptide to screen for ligands, agonists and antagonists of ADP-glucose receptor, or to purify the encoded polypeptide. For such applications bacterial cells, insect cells (e.g. Drosophila), yeast cells (e.g. *S. cerevisiae, S. pombe*, or *Pichia pastoris*), and vertebrate cells (e.g. mammalian primary cells and established cell lines; and amphibian cells, such as Xenopus embryos and oocytes), are useful, as well as crude or substantially purified cell membrane extracts from these cells. Exemplary cells of the invention useful for screening assays are CHO cells transiently transfected with pCDNA3.1 vector containing the nucleotide sequence designated SEQ ID NO:1, as described in the Example, below.

For applications in which G-protein coupled signaling through the receptor is assessed, the cells of the invention can further recombinantly express, either stably or transiently, one or more naturally occurring or chimeric Gα subunits that couple to the expressed ADP-glucose receptor polypeptide. As described previously, to ensure 1:1 stoichiometry of the receptor and its coupled G-protein, in such applications it may be desirable to recombinantly express the Gα subunit as a fusion polypeptide with the ADP-glucose receptor polypeptide.

As used herein, the term "recombinant expression" refers to transient or stable expression of a polypeptide from a recombinant nucleic acid molecule. Recombinant expression is advantageous in providing a higher level of expression of the polypeptide than is found endogenously, and also allows expression in cells or systems in which the polypeptide is not normally found. Exemplary cells of the invention that recombinantly express Gα subunits are CHO cells transiently cotransfected with a pCDNA3.1 vector containing the nucleotide sequence designated SEQ ID NO:1 and expression constructs encoding either or both of Gα16 and Gαqi3, as described in the Example, below.

The term "recombinant nucleic acid molecule" is intended to refer to a nucleic acid molecule that has been constructed, at least in part, by molecular biological methods, such as PCR, restriction digestion or ligation. A recombinant nucleic acid expression construct generally will contain a constitutive or inducible promoter of RNA transcription appropriate for the host cell or transcription-translation system, operatively linked to a nucleotide sequence that encodes the polypeptide of interest. The expression construct can be DNA or RNA, and optionally can be contained in a vector, such as a plasmid or viral vector. As described above, the nucleotide sequences of Gα subunits and methods of recombinantly expressing such subunits in a variety of cell types are well known in the art.

The cells of the invention can further recombinantly express, either stably or transiently, one or more promoter-reporter constructs in which expression of a reporter protein is induced in response to a G-protein coupled signal. Promoters responsive to G-protein coupled signals, and nucleotide sequences encoding reporter proteins (e.g. β-lactamase, luciferase, green fluorescent protein and β-galactosidase), are well known in the art, as are methods for constructing and expressing promoter-reporter constructs in a variety of cell types.

The cells of the invention can also contain one or more calcium indicators. Calcium indicators and their uses are well known in the art, and include compounds such as FLUO-3 AM, FLUO-4 AM, FURA-2, INDO-1, FURA RED, CALCIUM GREEN, CALCIUM ORANGE, CALCIUM CRIMSON, BTC, OREGON GREEN BAPTA, which are available commercially (e.g. Molecular Probes, Inc.), and described, for example, in U.S. Pat. Nos. 5,453, 517, 5,501,980 and 4,849,362. An exemplary calcium indicator useful in detecting G-protein coupled signaling through the ADP-glucose receptor is FLUO-4 AM, as described in Example I, below.

The invention further provides isolated polynucleotides that contain at least 20 contiguous nucleotides from the nucleotide sequence designated SEQ ID NO:1, or from the complement thereof. The polynucleotides of the invention are thus of sufficient length to be useful as sequencing primers, PCR primers and hybridization probes, and are also useful as therapeutic antisense reagents to inhibit ADP-glucose receptor expression. Optionally, the polynucleotides of the invention can also encode polypeptides having ADP-glucose receptor signaling activity, or peptides therefrom. Those skilled in the art can determine the appropriate length and sequence of a polynucleotide of the invention for a particular application.

As used herein, the term "polynucleotide" refers to a nucleic acid molecule that contains at least 20 contiguous nucleotides from the reference sequence and which may, but need not, encode a functional protein. Thus, a polynucleotide of the invention can contain at least 20, 22 or 25 contiguous nucleotides, such as at least, or not more than, 30, 40, 50, 60, 70, 80, 90, 100, 125, 150, 175, 200, 250, 300, 400, 500, 750, 1000 contiguous nucleotides from SEQ ID NO:1 or from its complement. A polynucleotide of the invention does not consist of the exact sequence of an EST present in publically available databases, including the sequences designated by GenBank Accession Nos. AI829607 (human); AA274112 (mouse); AA447306 (human); AW045980 (mouse); AW976204 (human); D81412 (human).

Figure 3:
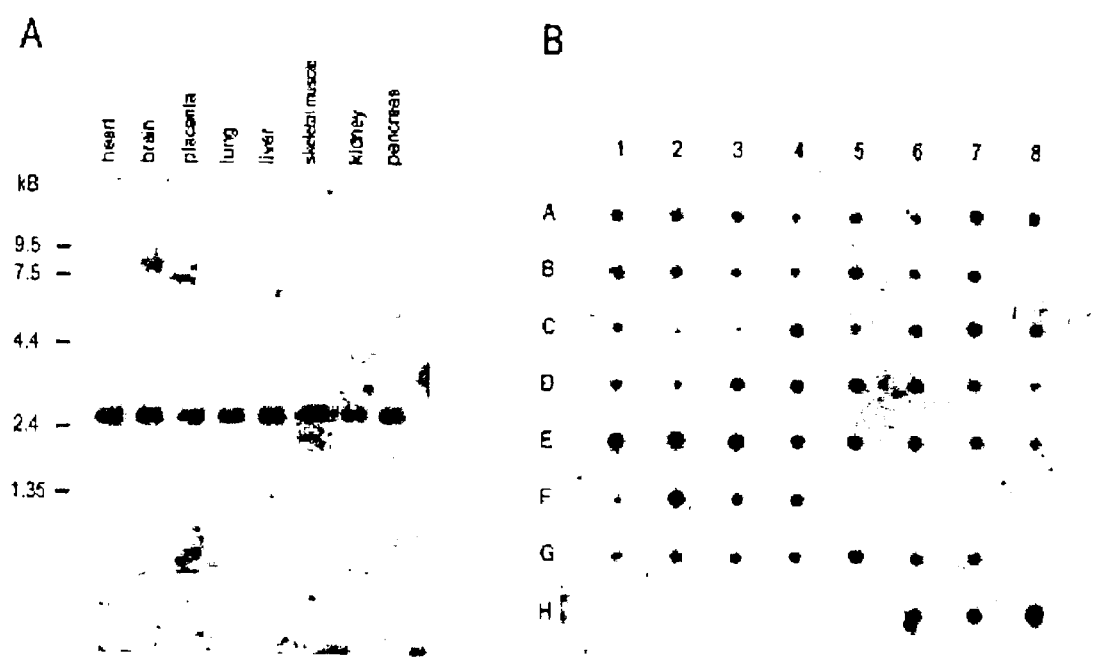
FIG. 3A is a Northern blot showing expression of ADP-glucose receptor mRNA in the indicated human tissues.
FIG. 3B is a dot blot showing expression of ADP-glucose receptor mRNA in the indicated human tissues: A1, whole brain; A2, amygdala; A3, caudate nucleus; A4, cerebellum; A5, cerebral cortex; A6, frontal lobe; A7, hippocampus; A8, medulla oblongata; B1, occipital lobe; B2, putamen; B3, substantia nigra; B4, temporal lobe; B5, thalamus; B6, nucleus accumbens; B7, spinal chord; C1, heart; C2, aorta; C3, skeletal muscle; C4, colon; C5, bladder; C6, uterus; C7, prostate; C8, stomach; D1, testis; D2, ovary; D3, pancreas; D4, pituitary gland; D5, adrenal gland; D6, thyroid gland; D7, salivary gland; D8, mammary gland; E1, kidney; E2, liver; E3, small intestine; E4, spleen; E5, thymus; E6, peripheral leukocytes; E7, lymph node; E8, bone marrow; F1, appendix; F2, lung; F3, trachea; F4, placenta; G1, fetal brain; G2, fetal heart; G3, fetal kidney; G4, fetal liver; G5, fetal spleen; G6, fetal thymus; G7, fetal lung; H1, yeast total RNA; H2, yeast tRNA; H3, *E. coli* rRNA; H4, *E. coli* DNA; H5, poly(rA); H6, human cot 1 DNA; H7, human DNA (100 ng); H8, human DNA (500 ng).

For certain applications, such as for detecting ADP-glucose receptor expression in a sample, it is desirable to use isolated polynucleotide molecules of the invention that specifically hybridize to a nucleic acid molecule encoding an ADP-glucose receptor. The term "specifically hybridize" refers to the ability of a nucleic acid molecule to hybridize, under stringent hybridization conditions as described below, to a nucleic acid molecule that encodes ADP-glucose receptor, without hybridizing to a substantial extent under the same conditions with nucleic acid molecules that do not encode ADP-glucose receptor, such as unrelated molecules that fortuitously contain short regions of identity with an ADP-glucose receptor sequence. Thus, a nucleic acid molecule that "specifically hybridizes" is of a sufficient length and contains sufficient distinguishing sequence from an ADP-glucose receptor to be characteristic of the ADP-glucose receptor. Such a molecule will generally hybridize, under stringent conditions, as a single band of about 2500 nucleotides on a Northern blot prepared from mRNA of human tissues (see FIG. 3A).

As used herein, the term "stringent conditions" refers to conditions equivalent to hybridization of a filter-bound nucleic acid molecule to a nucleic acid in a solution containing 50% formamide, 5× Denhart's solution, 5× SSC, 0.2% SDS at 42° C., followed by washing the filter in 0.1× SSC and 0.1% SDS at 65° C. twice for 30 minutes. Equivalent conditions to the stringent conditions set forth above are well known in the art, and are described, for example in Sambrook et al., *Molecular Cloning: A Laboratory Manual*, Cold Spring Harbor Laboratory, New York (1992).

The polynucleotides of the invention can, but need not, encode ADP-glucose receptor polypeptides. Thus, the invention polynucleotides can contain sequences from the 5' or 3' untranslated region of the nucleotide sequence designated SEQ ID NO:1, or contain coding sequences, or any combination thereof. The invention polynucleotides can be derived from either the sense or antisense strand of SEQ ID NO:1, or both.

The polynucleotides of the invention can also advantageously be used to direct the incorporation of amino acid additions, deletions or substitutions into a recombinantly expressed ADP-glucose receptor polypeptide, or the addition of restriction sites into SEQ ID NO:1. In such applications, it will be understood that the invention polynucleotides can contain nucleotide modifications with respect to SEQ ID NO:1, so long as it contains at least 20 contiguous residues from the reference sequence.

Exemplary polynucleotides of the invention are polynucleotides that contain a nucleotide sequence comprising nucleotides 1–20, 1–100, 101–120, 101–200, 201–220, 201–300, 301–320, 301–400, 401–420, 401–500, 501–520, 501–600, 601–620, 601–700, 701–720, 701–800, 801–820, 801–900, 901–920, 901–1000, 1001–1020, 1001–1100, 1101–1120 or 1100–1143 of SEQ ID NO:1 or of its complementary sequence.

The invention further provides a kit containing a pair of polynucleotides of the invention packaged together, either in a single container or separate containers. The pair of polynucleotides are preferably suitable for use in polymerase chain reaction (PCR) applications. Thus, the pair of polynucleotides can be used to detect or quantitate normal or abnormal expression of a nucleic acid molecule encoding an ADP-glucose receptor. The pair of polynucleotides can also be used to amplify a nucleic acid molecule encoding an ADP-glucose receptor, or any portion thereof, for sequencing, subcloning or for preparing modifications. The kit can further contain written instructions for use of the pair of polynucleotides in PCR applications, or solutions and buffers suitable for such applications.

In a preferred embodiment, the kit contains a polynucleotide containing a contiguous nucleotide sequence from the 5' untranslated region of SEQ ID NO:1, or its complement, and a polynucleotide containing a contiguous sequence from the 3' untranslated region of SEQ ID NO:1, or its complement, such that a nucleic acid molecule encoding a full-length ADP-glucose receptor can be amplified. An exemplary polynucleotide pair of the invention consists of SEQ ID NOS:5 and 6, as described in the example.

Isolated nucleic acid molecules which encode ADP-glucose receptor polypeptides, as well as the isolated polynucleotides described above, will be subsequently referred as "ADP-glucose receptor nucleic acid molecules." The isolated ADP-glucose receptor nucleic acid molecules of the invention can be prepared by methods known in the art. The method chosen will depend on factors such as the type and size of nucleic acid molecule one intends to isolate; whether or not it encodes a biologically active polypeptide (e.g. a polypeptide having ADP-glucose receptor activity or immunogenicity); and the source of the nucleic acid molecule.

An exemplary method for preparing an isolated ADP-glucose receptor nucleic acid molecule involves amplification of the nucleic acid molecule using ADP-glucose receptor-specific primers and the polymerase chain reaction (PCR). Using PCR, an ADP-glucose receptor nucleic acid molecule having any desired boundaries can be amplified exponentially starting from only a few DNA or RNA molecules, such as from a single cell of a species containing an ADP-glucose receptor gene. Suitable ADP-glucose receptor-specific primers can contain sequences derived from SEQ ID NO:1, or from sequences degenerate thereto. PCR methods, including methods of isolating homologs of a given nucleic acid molecule in another species using degenerate primers, are well known in the art.

Alternatively, an isolated ADP-glucose nucleic acid molecule can be prepared by screening a library, such as a genomic library, cDNA library or expression library, with a detectable ADP-glucose receptor nucleic acid molecule or antibody. Human libraries, and libraries from a large variety of mammalian species, are commercially available or can be produced from species or cells of interest. The library clones identified as containing ADP-glucose receptor nucleic acid molecules can be isolated, subcloned or sequenced by routine methods.

Furthermore, an isolated ADP-glucose nucleic acid molecule can be prepared by direct synthetic methods. For example, a single stranded nucleic acid molecule can be chemically synthesized in one piece, or in several pieces, by automated synthesis methods known in the art. The complementary strand can likewise be synthesized in one or more pieces, and a double-stranded molecule made by annealing the complementary strands. Direct synthesis is particularly advantageous for producing relatively short molecules, such as probes and primers, and also for producing nucleic acid molecules containing modified nucleotides or linkages.

The invention also provides an isolated ADP-glucose receptor polypeptide. The invention polypeptides are useful for a variety of applications, such as to identify ADP-glucose receptor ligands, agonists and antagonists, or as negative controls to confirm the specificity of known or presumptive ligands, agonists and antagonists of other G-protein coupled receptors. For such applications, the invention polypeptides are preferably contained within a composition containing a cell or artificial membrane, and components such as ADP-glucose or a G-protein. The invention polypeptides can also advantageously be used to prepare antibodies, which can be administered therapeutically as ADP-glucose receptor antagonists, or used as diagnostic reagents.

As used herein with respect to polypeptides and peptides, the term "isolated" indicates that the molecule is altered by the hand of man from how it is found in its natural environment. For example, an isolated ADP-glucose receptor polypeptide can be a molecule that is expressed from a recombinant nucleic acid molecule, such that it is present at a higher level than is normally found in a particular cell, or is present in a cell of a different type or species. Alternatively or additionally, an "isolated" ADP-glucose receptor polypeptide or peptide can be a "substantially purified" molecule, that is at least 60%, 70%, 80%, 90 or 95% free from cellular components with which it is naturally associated. An isolated polypeptide or peptide can be in any form, such as in a buffered solution, a suspension, a lyophilized powder, attached to a solid support, or in a cell membrane or artificial membrane (e.g. a liposome).

An isolated ADP-glucose receptor polypeptide can have at least 70% identity to the amino acid sequence designated SEQ ID NO:2. Preferably, the encoded polypeptide will have at least 75% identity, including at least 80%, 85%, 90%, 95%, 98%, 99% or greater identity to SEQ ID NO:2.

Also provided is an isolated immunogenic peptide having an amino acid sequence derived from SEQ ID NO:2. Such isolated immunogenic peptides are useful, for example, in preparing and purifying ADP-glucose receptor antibodies. The isolated immunogenic peptides of the invention can further be able to bind ADP-glucose, or to couple to G-proteins. Such immunogenic peptides can thus be used in assays to isolate ADP-glucose receptor ligands, agonists or antagonists, by the methods described herein. Additionally, such immunogenic peptides can act as antagonists to block signaling through the ADP-glucose receptor, by competing with ADP-glucose for binding to a ligand binding site, or by competing with a G-protein to bind to an effector binding site.

The term "immunogenic," as used herein, refers to a peptide that either is capable of inducing ADP-glucose receptor-specific antibodies, or capable of competing with ADP-glucose receptor-specific antibodies for binding to an ADP-glucose receptor. Peptides that are likely to be immunogenic can be predicted using methods and algorithms known in the art and described, for example, by Irnaten et al., Protein Eng. 11:949–955 (1998), and Savoie et al., Pac. Symp. Biocomput. 1999:182–189 (1999). The immunogenicity of the peptides of the invention can be confirmed by methods known in the art, such as by delayed-type hypersensitivity response assays in an animal sensitized to an ADP-glucose receptor polypeptide, or by direct or competitive ELISA assays.

An isolated immunogenic ADP-glucose receptor peptide can contain, or consist of, at least 10 contiguous residues from the amino acid sequence designated SEQ ID NO:2. Thus, an isolated immunogenic ADP-glucose receptor peptide can contain at least 10, such as at least 12, 15, 20, 25 or more contiguous amino acids of SEQ ID NO:2, including at least, or not more than, 30, 40, 50, 75, 100, 200, 300, 400 contiguous amino acids. Exemplary immunogenic ADP-glucose receptor peptides contain, or consist of, the amino acid sequence of amino acids 1–10, 1–50, 51–60, 51–100, 101–110, 101–150, 151–160, 151–200, 201–210, 201–250, 251–260, 251–300, 301–310 or 301–342 of SEQ ID NO:2.

For the production of antibodies that recognize ADP-glucose receptor in its native configuration, such peptides will preferably contain or consist of all, or part of, an extracellular or intracellular domain of SEQ ID NO:2. The extracellular domains of SEQ ID NO:2 are N-terminal to the first transmembrane region underlined in FIG. 1, and between the second and third, the fourth and fifth, and the sixth and seven transmembrane regions. The intracellular domains of SEQ ID NO:2 are between the first and second, third and fourth and fifth and sixth, transmembrane regions underlined in FIG. 1, and C-terminal to the seventh transmembrane region. Immunogenic peptides containing, or consisting of, all or part of a transmembrane region of SEQ ID NO:2, as underlined in FIG. 1, are also useful to raise antibodies for use in applications such as immunoblotting, where the ADP-glucose receptor need not be in its native configuration to be recognized.

Methods and compositions for recombinantly producing ADP-glucose receptor polypeptides, and peptides thereof having any desired boundaries, have been described above with respect to nucleic acid molecules, vectors and cells of the invention.

Alternatively, ADP-glucose receptor polypeptides and peptides can be prepared by biochemical procedures. As disclosed herein, ADP-glucose receptor polypeptide is widely expressed. Therefore, an isolated ADP-glucose receptor polypeptide can be substantially purified from mammalian tissues or cells which naturally express ADP-glucose receptor, or which recombinantly express ADP-glucose receptor, by biochemical procedures routinely used in the art, including membrane fractionation, chromatography, electrophoresis and ligand affinity methods. Additionally, an ADP-glucose receptor polypeptide can be substantially purified by immunoaffinity methods known in the art, using the ADP-glucose receptor antibodies described herein.

ADP-glucose receptor peptides can be produced by enzymatic or chemical cleavage of an ADP-glucose receptor polypeptide. Methods for enzymatic and chemical cleavage and for purification of the resultant peptide fragments are well known in the art (see, for example, Deutscher, Methods in Enzymology, Vol. 182, "Guide to Protein Purification," San Diego: Academic Press, Inc. (1990), which is incorporated herein by reference).

Furthermore, ADP-glucose receptor polypeptides and peptides can be produced by chemical synthesis methods known in the art. If desired, such as to optimize their functional activity, selectivity, stability or bioavailability, such molecules can be modified to include D-stereoisomers, non-naturally occurring amino acids, and amino acid analogs and mimetics. Examples of modified amino acids and their uses are presented in Sawyer, Peptide Based Drug Design, ACS, Washington (1995) and Gross and Meienhofer, The Peptides: Analysis, Synthesis, Biology, Academic Press, Inc., New York (1983), both of which are incorporated herein by reference. For certain applications, it can also be useful to incorporate one or more detectably labeled amino acids into a chemically synthesized polypeptide or peptide, such as radiolabeled or fluorescently labeled amino acids.

The isolated polypeptides and immunogenic peptides of the invention can optionally be conjugated to a carrier, such as KLH, serum albumin, tetanus toxoid and the like, using standard linking techniques, to enhance their immunogenicity. Additionally or alternatively, the isolated polypeptides and immunogenic peptides can be formulated with an adjuvant known in the art, such as Freund's complete or incomplete adjuvant.

For certain applications, such as to increase the stability or bioactivity of the molecule, or to facilitate its identification, an ADP-glucose receptor polypeptide or peptide can be chemically or enzymatically derivatized, such as by acylation, phosphorylation or glycosylation.

The invention also provides an antibody specific for an ADP-glucose receptor polypeptide, such as an antibody specific for a polypeptide having the amino acid sequence of SEQ ID NO:2. Also provided is an antibody specific for an isolated immunogenic peptide that contains at least 10 contiguous amino acids of an extracellular region of SEQ ID NO:2. The antibodies of the invention can be used, for example, to detect or distinguish between normal and altered expression of ADP-glucose receptor polypeptides in cells. Such antibodies are also useful for identifying nucleic acid molecules that encode ADP-glucose receptor polypeptides present in mammalian expression libraries, and for purifying ADP-glucose receptor polypeptides by immunoaffinity methods. Furthermore, such antibodies can be administered therapeutically as antagonists of the ADP-glucose receptor.

The term "antibody," as used herein, is intended to include molecules having specific binding activity for an ADP-glucose receptor of at least about $1 \times 10^5$ M$^{-1}$, preferably at least $1 \times 10^7$ M$^{-1}$, more preferably at least $1 \times 10^9$ M$^{-1}$. The term "antibody" includes both polyclonal and monoclonal antibodies, as well as antigen binding fragments of such antibodies (e.g. Fab, F(ab')$_2$, Fd and Fv fragments and the like). In addition, the term "antibody" is intended to encompass non-naturally occurring antibodies, including, for example, single chain antibodies, chimeric antibodies, bifunctional antibodies, CDR-grafted antibodies and humanized antibodies, as well as antigen-binding fragments thereof.

Methods of preparing and isolating antibodies, including polyclonal and monoclonal antibodies, using peptide and polypeptide immunogens, are well known in the art and are described, for example, in Harlow and Lane, *Antibodies: A Laboratory Manual*, Cold Spring Harbor Laboratory Press (1988). Non-naturally occurring antibodies can be constructed using solid phase peptide synthesis, can be produced recombinantly or can be obtained, for example, by screening combinatorial libraries consisting of variable heavy chains and variable light chains. Such methods are described, for example, in Huse et al. *Science* 246:1275–1281 (1989); Winter and Harris, *Immunol. Today* 14:243–246 (1993); Ward et al., *Nature* 341:544–546 (1989); Hilyard et al., *Protein Engineering: A practical approach* (IRL Press 1992); and Borrabeck, *Antibody Engineering*, 2d ed. (Oxford University Press 1995).

The invention also provides a method of identifying an ADP-glucose receptor agonist or antagonist. The method is practiced by contacting an ADP-glucose receptor polypeptide with one or more candidate compounds under conditions in which the ADP-glucose receptor produces a G-protein coupled signal in response to ADP-glucose, and identifying a candidate compound that alters production of the G-protein coupled signal. Such a compound is characterized as an ADP-glucose receptor agonist or antagonist. The agonists and antagonists identified by the methods of the invention are useful in therapeutic applications in which it is desirable to increase or decrease signaling through the ADP-glucose receptor.

An example of the method is described in Example I, below, in which an ADP-glucose receptor polypeptide, recombinantly expressed in CHO cells coexpressing Gα16 and Gαqi3, was contacted separately with ADP-glucose, CDP-glucose, GDP-glucose, UDP-glucose, TDP-glucose, ADP-ribose, ADP-mannose, AMP, ADP, ATP, and adenosine, to determine the ability of each compound to alter production of a G-protein coupled signal (ie. increase intracellular $Ca^{2+}$ concentration). By this assay, ADP-ribose was determined to be a partial agonist of ADP-glucose receptor (see FIG. 1A). The antagonistic effect of a compound can likewise be determined under the same exemplary conditions, but with the candidate compound added prior to addition of ADP-glucose at about its $EC_{50}$ concentration, and the effect of the candidate compound on inhibiting the agonist-induced increase in intracellular $Ca^{2+}$ concentration determined.

Another example of the method is described in Example II, below, in which guinea pig ileal tissue was contacted with ADP-glucose. A G-protein coupled signal through the ADP-glucose receptor in response to ADP-glucose can be evidenced either by inhibition of spontaneous contractions (FIG. 5A), inhibition of electrically-evoked contractions (FIG. 5B), or inhibition of histamine-induced contractions (FIG. 5C), without inhibition of muscarinic agonist-induced contractions. The effect of a candidate compound on ileal contractions can be determined by similar methods in order to determine whether the compound is an agonist or antagonist of the ADP-glucose receptor.

Figure 6:
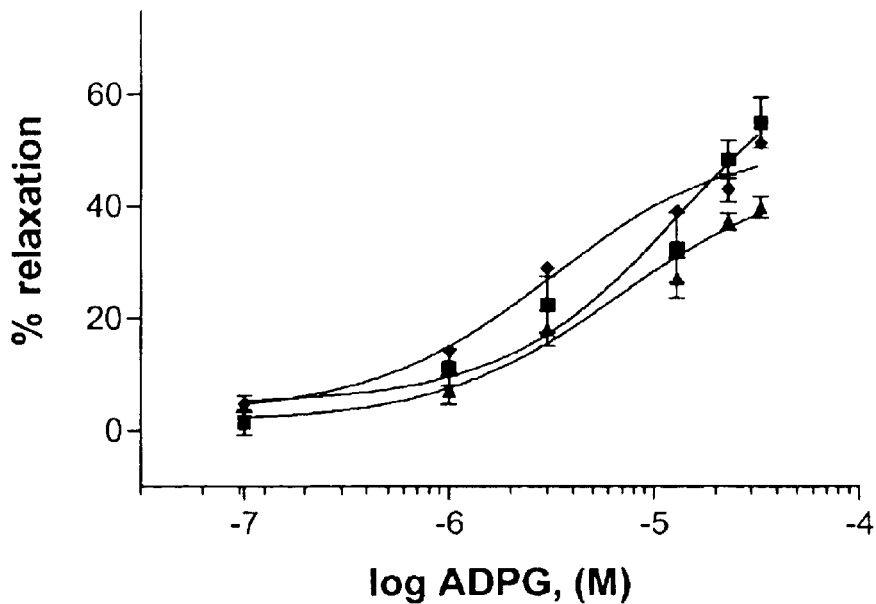
FIG. 6A shows the effect of ADP-glucose (ADPG) on contractions elicited by phenylephrine treatment of rat thoracic aorta (filled squares), abdominal aorta (filled triangles), and carotid artery (filled diamonds).
FIG. 6B shows the effect of ADP-glucose (ADPG) on contractions elicited by serotonin. All values are mean±S.E.M. and were determined in triplicate.
Figure 6:
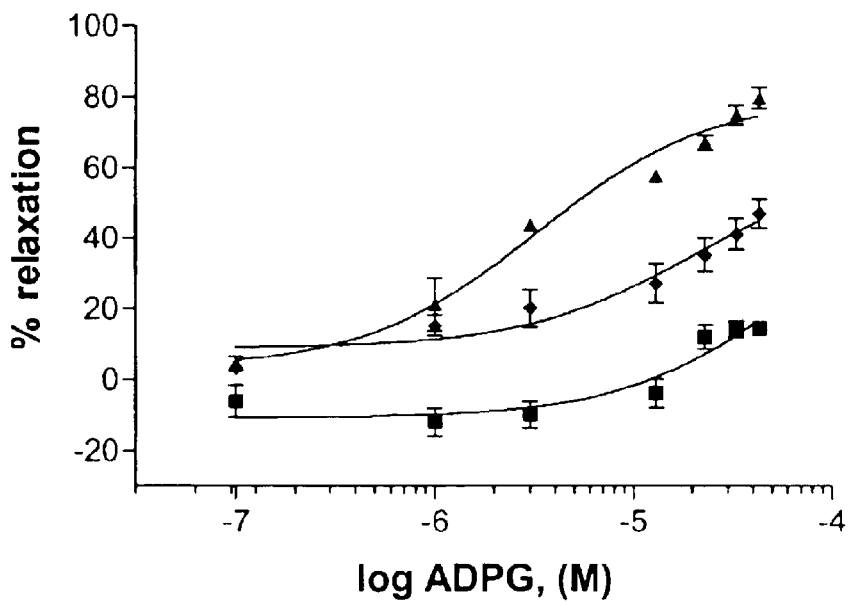

A further example of the method is described in Example III, below, in which rat arterial tissues were contacted with ADP-glucose. A G-protein coupled signal through the ADP-glucose receptor in response to ADP-glucose can be evidenced by inhibition of phenylephrine-evoked contractions (FIG. 6A) or inhibition of serotonin-evoked contractions (FIG. 6B). The effect of a candidate compound on contraction of rat arterial tissues can be determined by similar methods in order to determine whether the compound is an agonist or antagonist of the ADP-glucose receptor.

As used herein, the term "alter production of a G-protein coupled signal" refers either to an increase in production of the G-protein coupled signal above unstimulated levels, or above ADP-glucose-stimulated levels; or to a decrease in production of the G-protein coupled signal below unstimulated levels or below ADP-glucose-stimulated levels.

As used herein, the term "candidate compound" refers to any molecule that potentially acts as an ADP-glucose receptor agonist, antagonist or ligand in the screening methods disclosed herein. A candidate compound can be a naturally occurring macromolecule, such as a polypeptide, nucleic acid, carbohydrate, lipid, or any combination thereof. A candidate compound also can be a partially or completely synthetic derivative, analog or mimetic of such a macromolecule, or a small organic molecule prepared by combinatorial chemistry methods. If desired in a particular assay format, a candidate compound can be detectably labeled or attached to a solid support.

Methods for preparing large libraries of compounds, including simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., *Curr. Opin. Chem. Biol.* 2:422–428 (1998); Tietze et al., *Curr. Biol.*, 2:363–371 (1998); Sofia, *Mol. Divers.* 3:75–94 (1998); Eichler et al., *Med. Res. Rev.* 15:481–496 (1995); and the like. Libraries containing large numbers of natural and synthetic compounds also can be obtained from commercial sources.

The number of different candidate compounds to test in the methods of the invention will depend on the application of the method. For example, one or a small number of candidate compounds can be advantageous in manual screening procedures, or when it is desired to compare efficacy among several predicted ligands, agonists or antagonists. However, it is generally understood that the larger the number of candidate compounds, the greater the likelihood of identifying a compound having the desired activity in a screening assay. Additionally, large numbers of compounds can be processed in high-throughput automated screening assays. Therefore, "one or more candidate compounds" can be, for example, 2 or more, such as 5, 10, 15, 20, 50 or 100 or more different compounds, such as greater than about $10^3$, $10^5$ or $10^7$ different compounds.

As used herein, the term "ADP-glucose receptor agonist" refers to a molecule that selectively activates or increases normal signal transduction through the ADP-glucose receptor. An agonist can act by any mechanism, such as by binding the receptor at the normal ADP-glucose binding site, thereby mimicking ADP-glucose and promoting receptor signaling. An ADP-glucose receptor agonist can also act, for example, by potentiating the binding ability of ADP-glucose, or by favorably altering the conformation of the receptor. The methods of the invention can advantageously be used to identify an ADP-glucose receptor agonist that acts through any agonistic mechanism.

As used herein, the term "ADP-glucose receptor antagonist" refers to a compound that selectively inhibits or decreases normal signal transduction through the ADP-glucose receptor. An antagonist can act by any antagonistic mechanism, such as by binding to ADP-glucose or to ADP-glucose receptor, thereby inhibiting binding between ADP-glucose and its receptor. An ADP-glucose receptor antagonist can also act indirectly, for example, by modifying or altering the native conformation of ADP-glucose or its receptor. The methods of the invention can advantageously be used to identify an ADP-glucose receptor antagonist that acts through any antagonistic mechanism.

For therapeutic applications, an ADP-glucose receptor agonist preferably has an $EC_{50}$, and an ADP-glucose receptor antagonist preferably has an $IC_{50}$, of less than about $10^{-7}$ M, such as less than $10^{-8}$ M, and more preferably less than $10^{-9}$ M. However, depending on the stability, selectivity and toxicity of the compound, an ADP-glucose receptor agonist with a higher $EC_{50}$, or an ADP-glucose receptor antagonist with a higher $IC_{50}$, can also be useful therapeutically.

As described above, the particular G-protein coupled signal to detect in the assay methods is a matter of convenience, and will depend on the components of the assay system. For example, ADP-glucose receptor can couple to $G\alpha q$, $G\alpha i$ and $G\alpha 16$, but also can couple to a chimeric $G\alpha$ protein containing the C-terminal 5 residues of $G\alpha q$, $G\alpha i$ and $G\alpha 16$, with the remaining amino acids derived from any other $G\alpha$ of interest. Therefore, any second messenger signal transduced by the particular G-protein coupled to the ADP-glucose receptor in the assay system can be directly or indirectly detected.

Various assays and conditions suitable for identifying compounds that alter G protein coupled signaling are well known in the art, including high throughput automated screening assays. Assays that measure changes in intracellular $Ca^{++}$, cAMP, membrane voltage and gene expression are reviewed, for example, in Gonzalez et al., *Curr. Opin. in Biotech.* 9:624–631 (1998); Jayawickreme et al., *Curr. Opin. Biotech.* 8:629–634 (1997); and Coward et al., *Anal. Biochem.* 270:2424–248 (1999). Other appropriate assays include measurement of extracellular acidification, which can be monitored with a microphysiometer (e.g. Coldwell et al., *Br. J. Pharmacol.* 127:1696–1702 (1999)). In such assays, appropriate conditions for determining whether a compound is a ADP-glucose receptor agonist or antagonist are conditions in which ADP-glucose exhibits G-protein coupled signaling. The control assay can be performed before, after or simultaneously with the test assay.

G-protein signaling assays can involve first contacting the tissue, cell, extract or artificial assay system expressing ADP-glucose receptor with a detectable indicator. Calcium indicators, pH indicators, and metal ion indicators, and assays for using these indicators to detect and measure selected signal transduction pathways, are described, for example, in Haugland, *Molecular Probes Handbook of Fluorescent Probes and Research Chemicals*, Sets 20–23 and 25 (1992–94). Such assays can also involve transducing cells with a promoter-reporter nucleic acid construct such that expression of a detectable protein is coupled to signaling through the receptor. Suitable promoter-reporter systems have been described above, and are well known in the art.

Suitable assay systems for identifying compounds that alter G-protein coupled signaling include cells or tissues that naturally express, or recombinantly express, ADP-glucose receptor, so long as the ADP-glucose receptor can couple to a G-protein and induce a detectable signal in response to ADP-glucose and its agonists. Other suitable assay systems include crude or partially purified lysates or membrane extracts of such cells, and reconstituted artificial signaling systems. Artificial signaling systems can include, for example, a natural or artificial lipid bilayer, such as a liposome, to maintain ADP-glucose receptor in its natural configuration, and cellular fractions or isolated components necessary for transducing and detecting the desired G-protein coupled signal.

A variety of cell-based assay systems have been developed that are suitable for identifying compounds that alter G protein coupled signaling, including bacterial, yeast, Xenopus, baculovirus/insect cell and mammalian cell systems, and are reviewed, for example, in Tate et al., *Trends in Biotech.* 14:426–430 (1996). An exemplary yeast system, in which yeast strains are engineered to respond to agonist activation through G-protein coupled receptors with increased expression of a pheromone signaling pathway inducible FUS1-lacZ reporter gene, is described in Chambers et al., *J. Biol. Chem.* 275:10767–10771 (2000). Expression of the reporter gene in this system is readily monitored by a colorimetric assay. A further exemplary yeast system, in which yeast cells are engineered to respond to agonist activation of G-protein coupled receptors by histidine prototrophy, is described in Klein et al., *Nat. Biotech.* 16:1334–1337 (1998).

An exemplary Xenopus system suitable for measuring G-protein coupled activation of $G\alpha q$, $G\alpha i$ and $G\alpha s$ is based on visually detectable pigment dispersion or aggregation in transfected *X. laevis* melanophores, as described in Marchese et al., *Trends Pharmacol Sci.* 20:370–375 (1999). An alternative Xenopus system detects rises in intracellular calcium in response to agonist stimulation of G-protein coupled receptors by changes in calcium-dependent chloride conductance in transfected *X. laevis* oocytes, as described in Lynch et al., supra (1999).

A method of identifying ADP-glucose receptor agonists and antagonists can be performed either in the presence of a known ADP-glucose receptor agonist (e.g. ADP-glucose or ADP-ribose), or in the absence of agonist. When present, the agonist concentration is preferably within 10-fold of the $EC_{50}$ under the assay conditions. Thus, an agonist that competes with ADP-glucose or ADP-ribose for signaling through the ADP-glucose receptor, or indirectly potentiates signaling, can be readily identified. Likewise, an antagonist that prevents ADP-glucose or ADP-ribose from binding its receptor, or indirectly decreases signaling, can also be identified. Such compounds that demonstrate agonistic and antagonistic effects in the presence of ADP-glucose are particularly useful for therapeutic applications, in which physiological concentrations of circulatory ADP-glucose or ADP-ribose are likely to be present.

The invention also provides a method of identifying an ADP-glucose receptor ligand. The method is practiced by contacting an ADP-glucose receptor with one or more candidate compounds under conditions that allow selective binding between ADP-glucose receptor and ADP-glucose. A compound that selectively binds ADP-glucose receptor is characterized as an ADP-glucose receptor ligand.

As used herein, the term "ADP-glucose receptor ligand" refers to any biological or chemical compound that selectively binds an ADP-glucose receptor polypeptide. An "ADP-glucose receptor ligand" can further be an agonist or antagonist of ADP-glucose receptor, as described above, or can be a compound having little or no effect on ADP-glucose receptor signaling. In addition to applications described herein for agonists and antagonists, an ADP-glucose receptor ligand can be used, for example, to specifically target a diagnostic moiety to cells and tissues that express ADP-glucose receptor. Thus, an ADP-glucose receptor ligand can be labeled with a detectable moiety, such as a radiolabel, fluorochrome, ferromagnetic substance, or luminescent substance, and used to detect normal or abnormal expression of an ADP-glucose receptor polypeptide in an isolated sample or in in vivo diagnostic imaging procedures. Likewise, an ADP-glucose receptor ligand can be labeled with a therapeutic moiety, such as a cytotoxic or cytostatic agent or radioisotope, and administered in an effective amount to arrest proliferation or kill a cell or tissue that aberrantly expresses ADP-glucose receptor.

An ADP-glucose receptor ligand that "selectively binds" ADP-glucose receptor binds an ADP-glucose receptor polypeptide with high affinity, but does not bind, or binds with at least a 100-fold lower affinity, under the same conditions to a structurally related receptor that is not an ADP-glucose receptor, such as UDP-glucose receptor. Human UDP-glucose receptor designated KIAA0001 (GenBank accession no. D13626 (Q15391)) is described in Chambers et al., *J. Biol. Chem.* 275:10767–10771 (2000). High affinity binding to ADP-glucose receptor is evidenced by a dissociation constant (Kd) of less than about $10^{-4}$ M, preferably less than about $10^{-5}$ M, more preferably less than about $10^{-6}$ M, most preferably less than about $10^{-7}$ M.

Receptor binding assays, including high-throughput automated binding assays, and methods of determining Kd from such assays, are well known in the art, and any suitable direct or competitive binding assay can be used.

Exemplary high-throughput receptor binding assays are described, for example, in Mellentin-Micelotti et al., *Anal. Biochem.* 272:P182–190 (1999); Zuck et al., *Proc. Natl. Acad. Sci. USA* 96:11122–11127 (1999); and Zhang et al., *Anal. Biochem.* 268;134–142 (1999). The assay format can employ a cell, cell membrane, or artificial membrane system, so long as the ADP-glucose receptor is in a suitable conformation for binding ADP-glucose with a similarly affinity and specificity as an ADP-glucose receptor expressed on the surface of a mammalian cell.

Appropriate binding assays can involve detectably labeling a candidate compound, or competing an unlabeled candidate compound with detectably labeled ADP-glucose. As used herein, the term "detectably labeled" refers to derivation with, or conjugation to, a moiety that is detectable by any analytical means. An exemplary detectable moiety is a radioisotope (e.g. $^{14}C$, $^{131}I$, $^{32}P$ or $^{3}H$), fluorochrome (e.g. fluoroscein, green fluorescent protein), ferromagnetic substance, or luminescent substance. Methods of detectably labeling organic and inorganic compounds with such moieties are well known in the art. Detectably labeled ADP-glucose useful in the methods disclosed herein generally retains its ability to bind ADP-glucose receptor at concentrations within 10-fold of the $EC_{50}$ for unlabeled ADP-glucose.

Additionally, ligand binding can be assayed using fluorescence resonance energy transfer (FRET). For example, FRET can be used to detect transfer of fluorescence between a fluorescently labeled ADP-glucose receptor and either a fluorescently labeled ligand or a fluorescently labeled effector, upon binding of the ligand to the receptor (see, for example, Zhou et al., *Mol. Endocrinol.* 12:1594–1604 (1998)).

ADP-glucose itself, and the ADP-glucose receptor agonists (e.g. ADP-ribose) and antagonists identified using the methods and compositions described herein, are therapeutic compounds that can be administered to an individual, such as a human or other mammal, in an effective amount to increase or decrease signaling through the ADP-glucose receptor, and thus to prevent or ameliorate a ADP-glucose receptor associated condition.

As used herein, the term "ADP-glucose receptor-associated condition" refers to any abnormal physiological or psychological condition in which a quantitative or qualitative alteration in signaling through the ADP-glucose receptor contributes to the etiology or symptoms of the condition. An ADP-glucose receptor-associated condition also includes any physiological or psychological condition in which increasing or decreasing signaling through the ADP-glucose receptor has a beneficial effect in the individual.

As described herein, signaling through the ADP-glucose receptor leads to potent effects on contractile responses by smooth muscles. Therefore, ADP-glucose receptor-associated conditions include conditions in which it is desirable to modulate excitability and contractility of smooth muscles, either systemically or within specific organs or tissues.

For example, modulation of smooth muscle contractility is beneficial in modulating gastrointestinal function. Therefore, ADP-glucose receptor agonists or antagonists can be used to treat gastrointestinal disorders, such as diarrhea, gastritis, and inflammatory bowel disease, as well as for preoperative silencing of intestinal motility.

Additionally, smooth muscle tone is necessary for the function of vascular tissues. As described herein, signaling through the ADP-glucose receptor induces vasorelaxation in rat arterial tissue preparations. Therefore, the ADP-glucose receptor agonists or antagonists can be used to modulate vascular smooth muscle function by acting as vasoconstrictors or vasodilators. Conditions in which agents that act as vasoconstrictors or vasodilators are beneficial include disorders of cardiovascular function such as ischemia, hypertension, hypotension, angina pectoris, myocardial infarction, stroke, congestive heart failure, shock, erectile dysfunction, orthostatic intolerance, and migraine.

Consistent with the determination that signaling through the ADP-glucose receptor affects vascular function, it has recently been reported that cyclic perfusion of ADP-ribose, disclosed herein to be an ADP-glucose receptor agonist, in isolated frog heart induces a dose-dependent decrease in heart rate and contraction force, as well as a decrease in the action potential duration and rate of rise in the sinus node. Additionally, systemic administration of ADP-ribose to unanesthetised frogs induced a reversible increase in heart rate, likely due to sympathetic effects (Sosulina et al., *Ross Fiziol Zh Im I M Sechenova* 85:508–514 (1999); English abstract).

As described herein, signaling through the ADP-glucose receptor inhibits smooth muscle contractions induced by electrical stimulation, but not those induced by muscarinic agonist stimulation. Electrical stimulation of guinea pig ileum is known to lead to neuronal release of acetylcholine, which subsequently activates M3 muscarinic receptors on smooth muscle cells to produce contractions. Therefore, these results are consistent with signaling through the ADP-glucose receptor affecting acetylcholine release or function, rather than having a direct inhibitory effect on smooth muscle cells.

Acetylcholine has a variety of effects throughout the body. For example, acetylcholine is involved in vasodilation; eye iris contraction; contraction of the ciliary muscle of the eye; secretion from the salivary and lacrimal glands; bronchial constriction and secretion; gastrointestinal tone and secretion; gastrointestinal and urinary sphincter relaxation; and male erection. Therefore, agonists and antagonists of the ADP-glucose receptor can be involved in regulating such effects of acetylcholine. Acetylcholine has also been implicated in the pathogenesis of affective disorders, with the hypercholinergic state associated with depression, and the hypocholinergic state associated with mania. Therefore, agonists and antagonists of the ADP-glucose receptor can also be used to affect mood.

Additionally, signaling through the ADP-glucose receptor inhibits longitudinal muscle contractions induced by histamine. Histamine is known to be released from mast cells, and produces smooth muscle contractions by activating H1 histamine receptors located on smooth muscle cells. Therefore, signaling through the ADP-glucose receptor potentially inhibits histamine release by mast cells, or inhibits its effects on smooth muscle cells. Histamines have a variety of effects throughout the peripheral tissues and nervous system, including promoting vasodilation, vascular permeability, tachycardia, bronchospasm, inflammation, urticaria, anaphylaxis and asthma. Therefore, ADP-glucose receptor agonists and antagonists can be used in a manner similar to antihistamines to prevent or treat allergic, inflammatory, and respiratory conditions.

In view of the fact that ATP, which is formed by phosphorylation of ADP, and glucose, are the main sources of metabolic energy in most living organisms, a signaling molecule composed of ADP and glucose may signal to the organism the available energy resources. Accordingly, modulating signaling through the ADP-glucose receptor can be used to prevent or treat conditions associated with aberrant recognition or utilization of energy resources, such as disorders of glucose metabolism (e.g. glycogen storage disease, galactosemia), and disorders of body weight. Disorders involving increased body weight can be associated with overeating and/or endocrine dysfunction, and can trigger serious associated medical conditions, including hypertension, diabetes, cardiovascular disease and psychological maladjustments. Disorders involving decreased body weight include weight loss and wasting occurring during the course of a chronic disease such as cancer or AIDS, or as a result of a psychological condition such as in anorexia.

Additionally, ADP-glucose is known to be an important metabolite in bacteria during the synthesis of glycogen from ATP and glucose-1-phosphate. In mammals, however, glycogen is synthesized from UDP-glucose rather than ADP-glucose. Signaling through the ADP-glucose receptor may thus reflect the presence of bacterial pathogens, and be involved in host defense responses thereto (e.g. inflammation, fever, shock, aches, flu symptoms). Accordingly, ADP-glucose receptor agonists and antagonists can be used to prevent or treat conditions associated with infection by bacterial pathogens.

In plants and bacteria the formation of ADP-glucose is catalyzed by ADP-glucose pyrophosphorylase, which can also hydrolyze ADP-glucose depending on the concentration equilibrium. A related enzyme has recently been cloned from human and rat, termed YSA1H or NUDT5, which has a very similar tissue distribution of expression as ADP-glucose receptor (Gasmi et al., *Biochem. J.* 344:331–337 (1999); Yang et al., *J. Biol. Chem.* 275:8844–8853 (2000)). NUDT5 could therefore play a role in the synthesis or degradation of ADP-glucose and/or ADP-ribose as transmitters. Therefore, ADP-glucose receptor agonists and antagonists can be used to prevent or treat conditions associated with abnormal expression or function of YSA1H or NUDT5, and with physiological responses thereto.

ADP-glucose receptor is present on a 250 kb genomic fragment of chromosome 3 that contains the Usher syndrome type 3 (USH3) locus. Usher syndrome type 3 is an autosomal recessive disorder associated with progressive hearing loss and retinal degeneration. Therefore, ADP-glucose receptor is a candidate gene for the USH3 locus, and altered expression or function of the receptor may be causally associated with the syndrome. Accordingly, ADP-glucose receptor agonists and antagonists can be used to prevent or treat hearing loss, retinal degeneration, and other symptoms associated with Usher syndrome type 3.

Because of the widespread distribution of ADP-glucose receptor, a variety of conditions can be "ADP-glucose receptor-associated conditions" amenable to prevention or treatment by administration of an ADP-glucose receptor ligand, agonist or antagonist. Such conditions include, but are not limited to, conditions that affect the cardiovascular system, as described previously; immune system (e.g. immunodeficiency disorders, autoimmune disorders such as multiple sclerosis and rheumatoid arthritis, bacterial, fungal, protozoan and viral infections); respiratory system (e.g. respiratory distress system, asthma, pneumonia, bronchitis); kidney (e.g. glomerulonephritis, renal failure, lupus); hepatobiliary system (e.g. jaundice, cirrhosis, hepatitis); endocrine system (e.g. pituitary, thyroid, adrenal, reproductive dysfunctions); musculoskeletal system (e.g. osteoporosis, muscular dystrophies); and nervous system (e.g. neurodegenerative disorders, including Parkinson's disease, Huntington's disease, and Alzheimer's disease; pain; and psychiatric disorders, including depression, anxiety and schizophrenia, disorders of memory, attention and learning, and disorders of the sleep-wake cycle), as well as disorders that affect specific organs, such as benign and malignant tumors (e.g. breast cancer, lung cancer, colon cancer, skin cancer).

In one embodiment, the invention provides a method of ameliorating an ADP-glucose receptor associated condition by administering to an individual an effective amount of a therapeutic composition comprising ADP-glucose, or an ADP-glucose receptor agonist or antagonist. As described in Examples II and III, below, ADP-glucose induces inhibits contractile responses in guinea pig ileum and induces vasorelaxation in rat arterial tissues. Therefore, ADP glucose or an ADP-glucose receptor agonist or antagonist can be used, for example, to treat disorders involving smooth muscle contraction, including disorders of cardiovascular function, by inducing or inhibiting relaxation or constriction of the affected smooth muscle, as warranted by the particular condition.

The efficacy of a therapeutic compound of the invention in treating an ADP-glucose receptor associated condition can be determined using credible animal models of human disease, which are well known in the art, or using normal animals. For example, animal models of cardiovascular disorders, such as pulmonary hypertension, congestive heart failure, and the like, are available. The efficacy of a therapeutic compound in ameliorating a cardiovascular condition can be determined by administering the compound to the animal and determining the effect of the compound on an index of cardiovascular function correlated with the disease state, or the effect of the compound on ameliorating the disease state.

Exemplary indices of cardiovascular function that can be measured to determine the effect of a therapeutic compound include systemic arterial pressure, pulmonary arterial pressure, and heart rate. Such indices can be measured at a particular endpoint, or can be measured continuously. A radiotelemetry system, such as the system described in Mills et al., *J. Appl. Physiol.* 88:1537–1544 (2000), can advantageously be used to continuously monitor blood pressure and heart rate in freely moving animals, and thus to determine the effect of the therapeutic compound on such indices. Those skilled in the art understand which indices of function, and which animal models, are correlated with human ADP-glucose receptor associated conditions.

The therapeutic compounds of the invention can be formulated and administered in a manner and in an amount appropriate for the condition to be treated; the weight, gender, age and health of the individual; the biochemical nature, bioactivity, bioavailability and side effects of the particular compound; and in a manner compatible with concurrent treatment regimens. An appropriate amount and formulation for a particular therapeutic application in humans can be extrapolated based on the activity of the compound in the in vitro binding and signaling assays described herein, or from recognized animal models of the particular disorder, as described above.

The total amount of therapeutic compound can be administered as a single dose or by infusion over a relatively short period of time, or can be administered in multiple doses administered over a more prolonged period of time. Additionally, the compound can be administered in a slow-release matrice, which can be implanted for systemic delivery at or near the site of the target tissue. Contemplated matrices useful for controlled release of therapeutic compounds are well known in the art, and include materials such as DepoFoam™, biopolymers, micropumps, and the like.

The therapeutic compounds can be administered to an individual by routes known in the art including, for example, intravenously, intramuscularly, subcutaneously, intraorbitally, intracapsularly, intraperitoneally, intracisternally, intra-articularly, intracerebrally, orally, intravaginally, rectally, topically, intranasally, or transdermally. A preferred route for humans is oral administration.

Preferably, the therapeutic compounds are administered to a subject as a pharmaceutical composition comprising the compound and a pharmaceutically acceptable carrier. The choice of pharmaceutically acceptable carrier depends on the route of administration of the compound and on its particular physical and chemical characteristics. Pharmaceutically acceptable carriers are well known in the art and include sterile aqueous solvents such as physiologically buffered saline, and other solvents or vehicles such as glycols, glycerol, oils such as olive oil and injectable organic esters. A pharmaceutically acceptable carrier can further contain physiologically acceptable compounds that stabilize the compound, increase its solubility, or increase its absorption. Such physiologically acceptable compounds include carbohydrates such as glucose, sucrose or dextrans; antioxidants, such as ascorbic acid or glutathione; chelating agents; and low molecular weight proteins.

For applications that require the compounds and compositions to cross the blood-brain barrier, or to cross the cell membrane, formulations that increase the lipophilicity of the compound are particularly desirable. For example, the compounds of the invention can be incorporated into liposomes (Gregoriadis, *Liposome Technology*, Vols. I to III, 2nd ed. (CRC Press, Boca Raton Fla. (1993)). Liposomes, which consist of phospholipids or other lipids, are nontoxic, physiologically acceptable and metabolizable carriers that are relatively simple to make and administer.

The invention also provides methods of identifying an individual having or susceptible to an ADP-glucose receptor associated condition. Such knowledge allows optimal medical care for the individual, including appropriate genetic counseling and prophylactic and therapeutic intervention.

In one embodiment, the method is practiced by detecting a nucleic acid molecule which specifically hybridizes to the complement of SEQ ID NO:1 in a test sample. Abnormal expression of ADP-glucose receptor nucleic acid molecule in the sample, relative to a normal control sample, indicates that the individual has, or is susceptible to, an ADP-glucose receptor-associated condition.

As used herein, the term "abnormal expression" of an ADP-glucose receptor nucleic acid molecule refers to an increased or decreased amount of the nucleic acid molecule detected in the test sample relative to expression of SEQ ID NO:1 in a normal control sample. Altered abundance of a nucleic acid molecule can result, for example, from an altered rate of transcription, from altered transcript stability, or from altered copy number of the corresponding gene, and can be associated with point mutations, insertions, deletions, chromosomal translocations, splice variations and other rearrangements in the ADP-glucose receptor gene.

A variety of assays, and a variety of hybridization probes, including the isolated nucleic acid molecules and polynucleotides of the invention, can be used to detect a nucleic acid molecule which specifically hybridizes to the complement of SEQ ID NO:1 in a test sample. An appropriate assay format and probe to detect an alteration in the expression of an ADP-glucose receptor nucleic acid molecule can be determined depending on the alteration it is desired to identify.

Contemplated assays include, for example, in situ hybridization, which can be used to detect altered chromosomal location of the nucleic acid molecule, altered gene copy number, or altered RNA abundance, depending on the format used. Other assays include, for example, Northern blots and RNase protection assays, which can be used to determine the abundance and integrity of RNA; Southern blots, which can be used to determine the copy number and integrity of DNA; SSCP analysis, which can detect single point mutations in DNA, such as in a PCR or RT-PCR product; and direct sequencing of nucleic acid fragments, such as PCR amplification fragments. Methods of performing such assays are well known in the art. An exemplary assay, described in the Example, below, is a Northern blot assay, in which mRNA from a cell sample is probed with a detectably labeled nucleic acid molecule encoding SEQ ID NO:2 to determine expression of the endogenous ADP-glucose transcript.

In another embodiment, the method is practiced by detecting a polypeptide which specifically binds an ADP-glucose receptor ligand in a test sample. Abnormal expression of an ADP-glucose receptor polypeptide in the sample indicates that the individual has or is susceptible to an ADP-glucose receptor-associated condition.

As used herein, the term "abnormal expression" of an ADP-glucose receptor polypeptide refers to an increased or decreased amount, altered subcellular localization, altered structure, or altered signaling activity, of the detected polypeptide in a test sample relative to that of SEQ ID NO:2 in a normal control sample. Altered abundance of a polypeptide can result from altered rate of translation or altered copy number of the corresponding transcript, or from altered stability of the protein. Altered subcellular localization can result from truncation or inactivation of a sorting sequence, from fusion with another polypeptide sequence, or altered interaction with other cellular polypeptides. Altered structure, as well as altered abundance, localization or activity of the polypeptide, can result from chromosomal deletions and other mutations, as well as from altered expression of cellular effector molecules.

A variety of assays, and a variety of ligand probes can be used to detect expression of an ADP-glucose receptor in a test sample. Exemplary ligand probes include the antibodies of the invention, detectably labeled ADP-glucose or ADP-ribose, and the agonists, antagonists and ligands identified by the methods described herein. The choice of assay format and ligand probe will depend on the alteration it is desired to identify.

Contemplated assays to detect expression of a polypeptide in a sample include in situ histochemistry, immunoblotting, immunoprecipitation, FACS analysis, radioligand binding, and ELISA analysis. Such assays can be direct, using a detectably labeled ligand, or indirect, using a labeled secondary reagent, such as an anti-ligand antibody. Exemplary labels include fluorescent labels, enzymes, radioisotopes, and biotin. Detection can be by any convenient analytical means, including by spectrophotometric, radiographic or chemiluminescent means, depending on the assay.

Assays to determine G-protein coupled signaling activity of ADP-glucose receptor have been described above in connection with screening assays to identify ADP-glucose receptor agonists and antagonists. Similar assays can be used to compare activity of an ADP-glucose receptor polypeptide in a test sample with activity of the polypeptide designated SEQ ID NO:2 in a normal control sample.

As described above, ADP-glucose receptor is a candidate gene for the Usher syndrome type 3 locus. Whether or not there is a causal link between ADP-glucose receptor and USH3, detection of ADP-glucose receptor integrity or expression can be used as a marker for the integrity of the chromosomal region flanking the USH3 locus, and thus serve as an indicator of propensity for development of USH3.

As used herein, the term "sample" refers to any biological fluid, cell, tissue, organ or portion thereof, that is appropriate to detect ADP-glucose receptor nucleic acids and polypeptides, and includes samples present in an individual as well as samples obtained or derived from the individual. For example, a sample can be a histologic section of a specimen obtained by biopsy, or cells that are placed in or adapted to tissue culture. A sample further can be a subcellular fraction or cell extract, or a crude or substantially pure nucleic acid or protein preparation.

The appropriate source and method of preparing the sample can be determined by those skilled in the art, depending on the application of the detection method. For example, in order to detect structure of genomic DNA encoding ADP-glucose receptor, any convenient source of DNA, such as blood cells, lymph cells, cheek cells or skin cells, can be used. However, to detect expression of ADP-glucose receptor mRNA or protein, or determine receptor activity, a sample should be obtained from a tissue that expresses ADP-glucose receptor.

The following examples are intended to illustrate but not limit the present invention.

EXAMPLE I

Cloning and Pharmacological Characterization of Human ADP-Glucose Receptor

This example shows the cloning and characterization of a novel receptor that specifically transduces G-protein coupled signals in response to ADP-glucose.

Cloning of the Human ADP-Glucose Receptor

Based on the recent identification of a G-protein coupled receptor for UDP-glucose (Chambers et al., *J. Biol. Chem.* 275:10767–10771 (2000)), it was predicted that related sugar-nucleoside receptors exist in the human genome. Accordingly, the amino acid sequence of the UDP-glucose receptor (KIAA0001; GenBank accession no. D13626 (Q15391)) was searched against human genomic DNA sequences in GenBank using the TBLASTN algorithm (Altschul et al., *J. Mol. Biol.* 215:403–410 (1990)). A human genomic clone (accession no. AC024886) was identified that exhibited 47% identity and 66% overall homology to the query sequence. The receptor gene appears to be intronless since a contiguous open reading frame was present at the genomic level.

The genomic fragment containing the receptor gene was amplified by two rounds of nested PCR (first round primers: 5' ATGGAGGGGAAGCTAGAGAAGAGT (SEQ ID NO:3) and 5' TAGCGCTTTGCTTTAACGAGTTC (SEQ ID NO:4); second round primers: 5' ACTG AAGCTTTAGGCTGAAAATAACCATCCTCTC (SEQ ID NO:5) including a HindIII restriction site (underlined) and 5' CGACTCGAGTAGCGCTTTGCTTTAACGAGTTC (SEQ ID NO:6) including an XhoI restiction site (underlined). The resulting product was cloned into the mammalian expression vector pCDNA3.1(+)-Neo (Invitrogen) and sequenced.

The 1143 bp nucleotide sequence of the amplified product (SEQ ID NO:1), and the deduced 342 amino acid sequence of the encoded polypeptide (SEQ ID NO:2), are shown in FIG. 1. The translated protein contains characteristic features of a G-protein coupled receptor, including 7 hydrophobic domains, the "DRY" motif at the C-terminal end of the predicted third transmembrane domain and a number of conserved proline and asparagine residues found in virtually all G-protein coupled receptors.

Multiple sequence alignments and phylogenetic trees were constructed with MegAlign (DNAStar, Madison, Wis.) using the CLUSTAL algorithm. Based on this analysis, other closely related G-protein coupled receptors include receptors for platelet-activating factor (32% identity; 50% homology), thrombin (23%; 44%), the orphan receptors H963 (33%; 52%), GPR34 (31%; 47%) and the putative purinoreceptors P2Y10 (28%; 43%) and P2Y9 (27%; 49%).
Characterization of the Cloned Human ADP-Glucose Receptor and of the ADP-Glucose Receptor Endogenously Expressed in HEK 293 Cells In order to characterize the function of the encoded receptor, the pCDNA3.1 expression construct containing the amplified receptor gene was transiently transfected into human embryonic kidney (HEK 293) cells or Chinese hamster ovary (CHO) cells. HEK 293 cells were cultured in DMEM containing 10% fetal bovine serum (FBS), and CHO cells were cultured in alpha-MEM with 5% FBS. All cells were kept at 37° C. in a 5% $CO_2$ atmosphere.

For certain experiments, the cells were transiently cotransfected with the receptor construct and equimolar ratios of the G-protein alpha subunit Gα16 and/or the chimeric subunit Gαi3 in pCDNA3.1 (described in Saito et al., *Nature* 265–269 (1999)). For functional assays measuring intracellular calcium, twenty-four hours after transfection, cells were seeded into black clear-bottom 96-well plates at a density of 50,000 cells/well. Following overnight incubation the cells were loaded for 1 h with 1 μM of the fluorescent calcium indicator dye Fluo4-AM (Molecular Probes) dissolved in assay buffer containing Hank's balanced salts, 20 mM HEPES, 1% FBS, 2.5 mM probenecid, pH 7.4. After loading, the cells were washed three times with assay buffer without FBS. Addition of drugs and measurement of changes in intracellular calcium were performed using a fluorimetric imaging plate reader (FLIPR, Molecular Devices). Agonist responses were determined using the maximum change in fluorescence over baseline.

To enforce coupling of the novel receptor to the phospholipase C pathway, CHO cells were transiently cotransfected with expression constructs containing the amplified receptor DNA, Gα16 and a chimeric Gαq subunit carrying the C-terminal tail of Gαi3. From among ADP-glucose, CDP-glucose, GDP-glucose, UDP-glucose, TDP-glucose, ADP-ribose, AMP, ADP, ATP, and adenosine (all obtained from Sigma), and ADP-mannose (a gift of Drs. H. Yang and J. H. Miller, University of California, Los Angeles), only ADP-glucose and ADP-ribose induced a dose-dependent and transient increase in intracellular $Ca^{2+}$ ($[Ca^{2+}]_i$) levels in transfected but not in untransfected cells.

As shown in FIG. 2, ADP-glucose induced a transient increase in $[Ca^{2+}]_i$ with an $EC_{50}$ of 2.98±0.22 µM in CHO cells transiently transfected with the receptor construct together with Gα16 and Gαqi3 (FIG. 2A, filled squares). The closely related molecule ADP-ribose could also activate the transfected receptor specifically, although less potently in the same assay (FIG. 2A, open circles; $EC_{50}$=59.4±7.3 µM). ADP-mannose was unable to activate the receptor, although mannose and glucose are epimers, differing only in the spatial orientation of one hydroxyl group. Dose-response curves were calculated using GraphPad Prism (GraphPad Software Inc.).

In order to determine the preferential G-protein coupling of the ADP-glucose receptor, mobilization of $[Ca^{2+}]_i$ was examined in CHO cells expressing either the receptor alone or in combination with either Gα16 or Gαqi3. In cells cotransfected with the ADP-glucose receptor and Gαqi3, ADP-glucose activated the receptor with an $EC_{50}$ of 8.2±1.3 µM, whereas the combination of ADP-glucose receptor with Gα16 showed an $EC_{50}$ of 11.8±2.4 µM. CHO cells expressing ADP-glucose receptor alone still displayed mobilization of intracellular $Ca^{2+}$ upon stimulation with ADP-glucose, with an $EC_{50}$ value was only 24.0±4.1 µM.

These results indicate that the ADP-glucose receptor naturally couples to both the Gαq- and Gαi-type of G proteins, but can also interact with Gα16. Coexpression of multiple G alpha subunits can increase the efficacy of of the agonist ADP-glucose to couple to second messenger systems in a synergistic manner, thus lowering the observed $EC_{50}$ value.

The ADP-glucose receptor construct was also expressed in HEK 293 cells. However, upon stimulation with ADP-glucose, untransfected HEK 293 cells exhibited a strong mobilization of $[Ca^{2+}]_i$ which was indistinguishable from transfected cells. It was therefore concluded that HEK 293 cells express an endogenous G-protein coupled receptor specific for ADP-glucose. HEK 293 cells did not respond to any of the other nucleoside-glucose compounds tested (ie. CDP-glucose, GDP-glucose, UDP-glucose or TDP-glucose) with an increase in $[Ca^{2+}]_i$.

In HEK 293 cells, stimulation of the endogenous ADP-glucose receptor with ADP-glucose increased with an $EC_{50}$ of 2.90±0.51 µM (FIG. 2B, filled squares). Transient cotransfection of HEK 293 cells with the construct encoding the cloned ADP-glucose receptor together with Gα16 did not produce a significant change in potency of ADP-glucose to stimulate intracellular $Ca^{2+}$ release ($EC_{50}$=2.50±0.82 µM), indicating that the endogenous ADP-glucose receptor in HEK 293 cells might be identical to, or substantially similar to, the cloned receptor.

In contrast to CHO cells, ADP-ribose behaved as a full agonist and potently increased in HEK 293 cells with an $EC_{50}$ of 38.7±10.6 µM (FIG. 2B, open circles). This discrepancy could reflect the different subsets of G proteins expressed in the two cell lines, enabling a more efficient coupling of the receptor in HEK 293 versus CHO cells.

Tissue Distribution of Expression of Human ADP-Glucose Receptor

In order to assess expression and distribution of ADP-glucose receptor in human tissues, a probe having the nucleotide sequence designated SEQ ID NO:1 was random-prime labeled with $^{32}$P-dCTP and used to hybridize to northern blots and dot blots under stringent conditions. Total RNA from HEK 293 cells was prepared using Trizol reagent (Life Technologies). Thirty µg of HEK 293 total RNA were separated on a 1% agarose gel containing formaldehyde and transferred onto Hybond N membranes (Amersham-Pharmacia Biotech). A Multiple Tissue Northern Blot (MTN™), and a Human RNA Master Blot™ dot blot containing normalized amounts of mRNA from various human tissues were obtained from Clontech. Blots were hybridized at 65° C. overnight. Final stringent washing was performed in 0.1× SSC (0.15 M NaCl, 0.015 M sodium citrate), 0.1% sodium dodecylsulfate (0.15 M NaCl, 0.015 M sodium citrate) at 65° C.

In HEK 293 cells, an mRNA species of about 2500 nucleotides hybridized under stringent conditions with the cloned ADP-glucose receptor cDNA probe. This result is consistent with an interpretation that HEK 293 cells express an ADP-glucose receptor having the same or substantially similar sequence as the cloned receptor.

Hybridization to the human tissue Northern blot (FIG. 3A) and human tissue dot blot (FIG. 3B) under stringent conditions revealed ubiquitous expression of ADP-glucose receptor mRNA. Highest levels of expression were detected in liver, pituitary, adrenals, small intestine, pancreas and kidney. Moderate levels of expression were observed in all brain regions analyzed. Weaker hybridization signals were detected in bladder, aorta and skeletal muscle. The different relative signal intensities between the two blots (e.g. for skeletal muscle) could be due to the different normalization procedures (ie. the Northern blot mRNAs were normalized to equal loading of β-actin mRNA, whereas the dot blot mRNAs were normalized against eight different housekeeping genes).

EXAMPLE II

Physiological Effects Mediated by Signaling Through the ADP-Glucose Receptor

This example shows the physiological effects of ADP-glucose in guinea pig ileum.

The ADP-glucose receptor appeared to be highly expressed in small intestine. Therefore, the effects of ADP-glucose on contractile activity and evoked contractions in guinea pig ileum were examined.

Ileal segments (about 2 cm) were prepared from male guinea pigs euthanized by asphyxiation with $CO_2$ and mounted in an organ bath filled with Krebs-Ringer bicarbonate (KRB) buffer as described in Thomas et al., Mol. Pharmacol. 44:102–110 (1993). Isometric contractions of the preparations were measured with a force transducer and recorded on a polygraph (Grass Instruments). The contractile responses are expressed as the mass (g) required to generate the measured force. For contractile measurements of field-stimulations, ilea were mounted between platinum ring electrodes connected to a stimulator (Grass SD9). Ilea were electrically stimulated (40 mV, 8 ms duration, 0.2 Hz) for 5 min followed by a resting period of 8–10 min.

Drugs were diluted in KRB and added directly to the bath. For intraluminal drug application a polyethylene tube (I.D.: 2 mm; length: 1.2 cm) was inserted about 3 mm deep into the ileum and fixed with a surgical thread. The other end of the preparation was closed tightly by a thread. The intubated ilea were mounted in the organ bath in such a way that the open end of the polyethylene tube was extending above the buffer surface. Drugs were administered to the ileal lumen using a Hamilton syringe. After each incubation, ilea were washed three times with KRB and allowed to equilibrate for at least 10 min. For some experiments ilea were removed from animals that had been treated with 100 $\mu$g/kg pertussis toxin three days prior to the experiment. Dose response curves were obtained in separate experiments for each drug concentration tested in duplicate and $EC_{50}$ values were calculated using GraphPad Prism.

Figure 4:
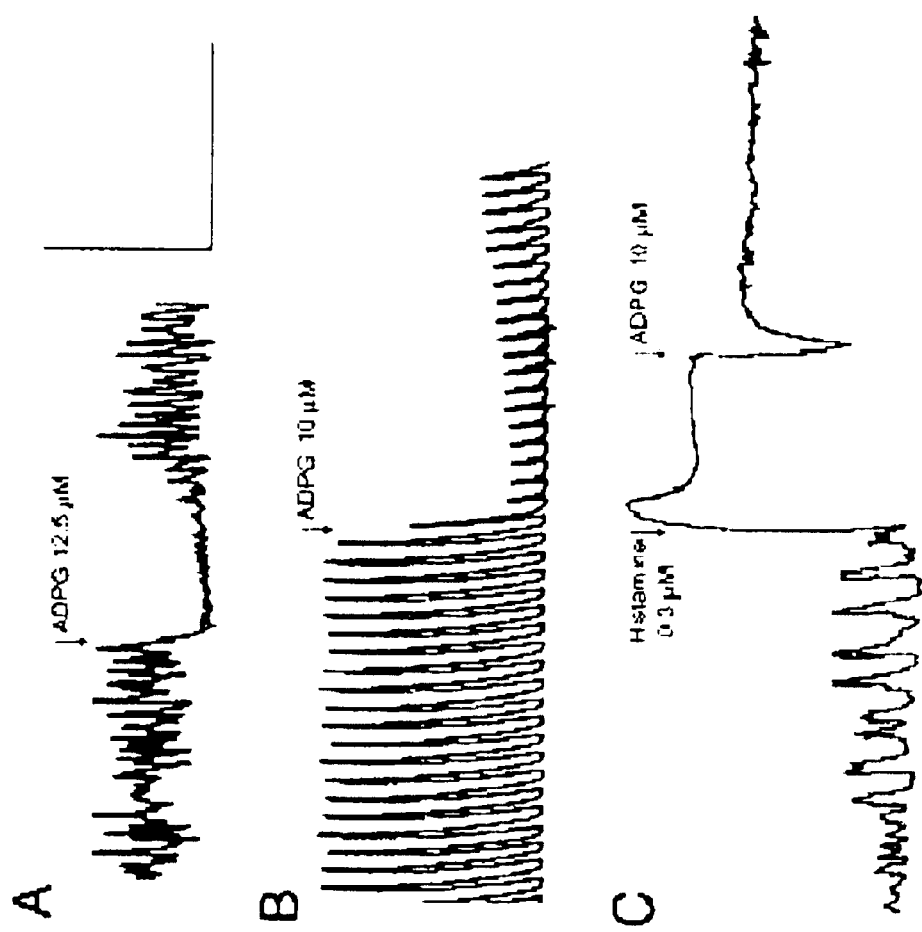
FIG. 4A shows the effect of ADP-glucose on spontaneous contractions in guinea pig ileal segments.
FIG. 4B shows the effect of ADP-glucose on electrically-evoked contractions in guinea pig ileal segments.
FIG. 4C shows the effect of ADP-glucose on histamine-induced contractions in guinea pig ileal segments. Arrows denote time points of drug addition and values are given as final bath concentrations. The vertical scale bar equals contractile force measured as mass. Recorder settings were (A) 0.5 g, (B) 1 g and (C) 2 g. The horizontal scale bar equals 1 min in A, B and C.

In a series of initial experiments it was observed that addition of ADP-glucose caused inhibition of spontaneous contractions in the ileum preparations (FIG. 4A). However, due to the irregular nature of these contractions it was not possible to study dose-response relationships of pharmacological agents in such a preparation. Therefore, field-stimulation was used to elicit contractions that are known to be mediated by neuronal release of acetylcholine activating M3 muscarinic receptors (Cowie et al., *Brit. J. Pharmacol.* 64:565–580 (1978); Kilbinger et al., *Eur. J. Pharmacol.* 103:313–320 (1984)).

Figure 5:
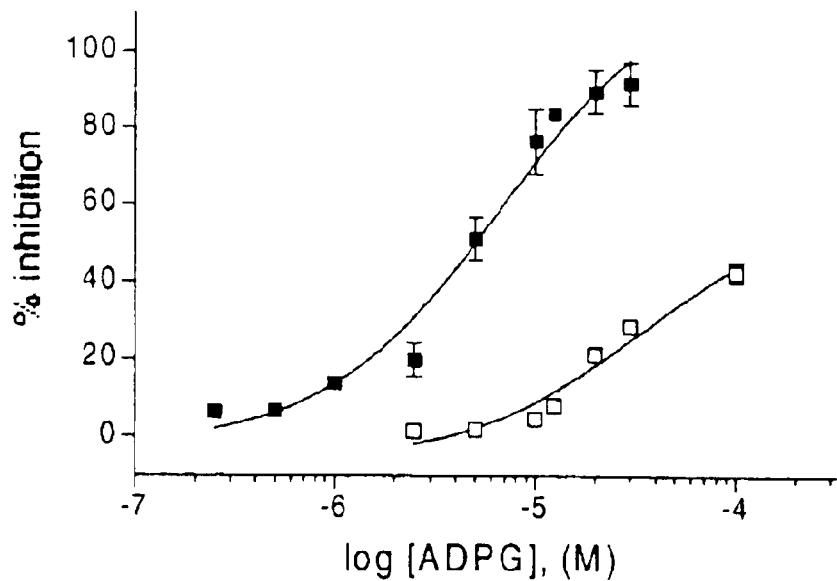
FIG. 5A shows the effect of ADP-glucose (ADPG) on contractions elicited by field-stimulation of untreated guinea pig ileum (filled squares) and pertussis toxin-treated ileal preparations (open squares).
FIG. 5B shows the effect of ADP-glucose (ADPG) on contractions produced by 0.3 µM histamine. All values are mean±S.E.M. and were determined in duplicate.
Figure 5:
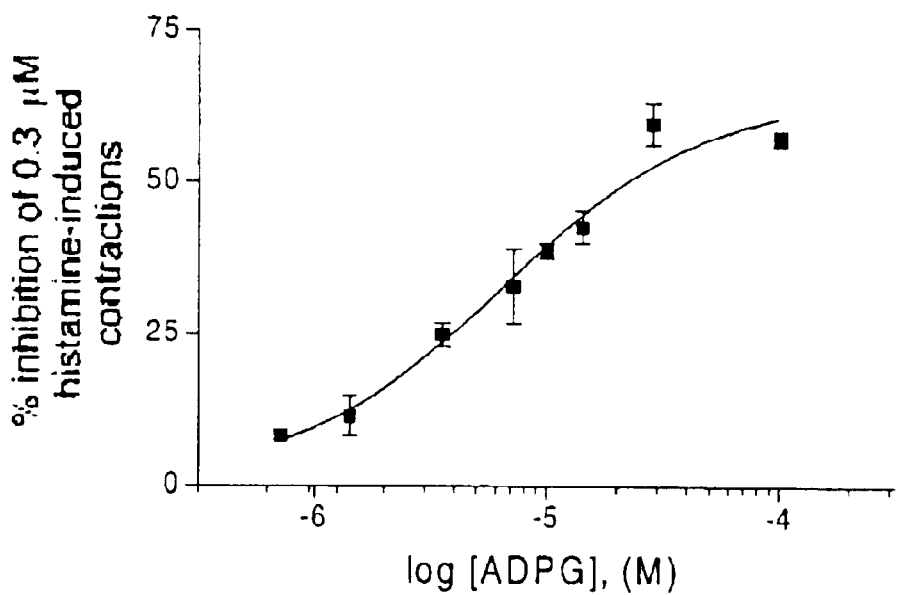

ADP-glucose dose-dependently inhibited electrically evoked contractions with an $EC_{50}$ value of 6.64±0.4 $\mu$M (FIGS. 4B and 5A). Maximally effective concentrations of ADP-glucose produced 90% inhibition. ADP-ribose produced very similar inhibitory effects on electrically-evoked contractions in these preparations, whereas other nucleoside-diphosphoglucoses were ineffective.

Pertussis toxin treatment greatly reduced the potency of ADP-glucose to inhibit electrically evoked contractions of guinea pig ileum preparations. As shown in FIG. 5A, maximal inhibition was reduced to 40% and the $EC_{50}$ value increased to 35.5±5.5 $\mu$M after pertussis toxin treatment. These results suggest that a signal transduction pathway requiring Gi/o-type G proteins are involved in the inhibition of contractile activity by ADP-glucose in the guinea pig ileum.

ADP-glucose occurs abundantly in plants and bacteria. Therefore, it was investigated whether food or intestinal bacteria could be a source of ADP-glucose that would in turn influence intestinal motility by signaling through the ADP-glucose receptor. Using a specialized setup for intraluminal administration of drugs, no effect of ADP-glucose on field-stimulated contractions could be detected. However, when the ileal preparations were punctured to release intraluminal content into the bath at the end of the observation period, a strong inhibition of electrically-evoked contractions could be readily observed. It thus appears that, although the intraluminal ADP-glucose had not been metabolized, it was not able to reach the smooth muscle layer and the surrounding neural plexus by diffusion or other transport mechanisms.

Acetylcholine and histamine are the most studied transmitters to stimulate contractions of longitudinal smooth muscles in the guinea pig ileum (Cowie et al., *Brit. J. Pharmacol.* 64:565–580 (1978); Marquardt, *Clin. Rev. Allergy* 1:343–351 (1983)). As shown in FIGS. 4C and 5B, respectively, ADP-glucose dose-dependently inhibited histamine-evoked contractions in guinea pig ileum preparations with an $EC_{50}$ value of 6.2±1.8 $\mu$M and a maximal inhibition of 60%. In contrast, contractions produced by the muscarinic agonist oxotremorine M were unaffected by ADP-glucose.

Taken together, these results indicate that ADP-glucose, acting through the ADP-glucose receptor, inhibits contractile responses in guinea pig ileum, and that this effect is likely mediated by specific neuronal pathways rather than through a direct effect on smooth muscle cells.

EXAMPLE III

Vasorelaxation of Rat Arterial Tissues Mediated by Signaling Through the ADP-Glucose Receptor This example shows the physiological effects of ADP-glucose in rat arterial tissues.

The ADP-glucose receptor was shown to inhibit contractile response in guinea pig ileum and to be expressed in aorta. Therefore, the effects of ADP-glucose on contractile activity in rat abdominal aorta, thoracic aorta and carotid arteries were examined.

Rat arterial tissues were prepared as described previously (Duckles, S. P., *J. Pharmacol. Exp. Ther.* 240: 697–700 (1987); Sara Sangha et al., *J. Appl. Physiol.* 88: 507–517 (2000)). Briefly, male Wistar rats (250 g) were sacrificed by decapitation. The thoracic and abdominal aorta and the carotid artery were immediately removed and cleaned of adhering tissue. Arteries were cut into rings (about 3 mm in length) and mounted into an organ bath filled with Kreb-Ringer-bicarbonate buffer at 37° C. (buffer composition: 119.2 mM NaCl, 25 mM $NaHCO_3$, 4.9 mM KCl, 1.2 mM $MgSO_4$, 11.1 mM glucose, 0.114 mM ascorbic acid, pH 7.4). The buffer was aerated by bubbling with 95% $O_2$:5% $CO_2$. Arterial rings were connected to a force transducer and isometric contractions of the preparations were recorded using MacLab. The contractile responses are expressed as the mass (g) required to generate the measured force. The arterial preparations were equilibrated for one hour at a resting force of 2 g and then challenged several times with 100 mM KCl to establish a baseline.

To determine the effect of ADP-glucose on evoked contractions, arterial rings were precontracted with either 0.3 $\mu$M phenylephrine or 0.3 $\mu$M serotonin. ADP-glucose was subsequently added to the arterial rings in a cumulative manner to establish a dose-response relationship between ADP-glucose concentration and arterial ring contraction. At the end of each experiment, residual constriction was reversed by the addition of 1 $\mu$M acetylcholine. Each arterial preparation was tested in triplicate with each cumulative dosage scheme carried out at least twice. Data are expressed as means±S.E.M. and dose-response curves were calculated with Prism (GraphPad, San Diego).

FIG. 6A shows that ADP-glucose-induced relaxation of phenylephrine-precontracted arterial preparations occurs in a dose-dependent manner. Half maximal effective concentrations (EC50) of ADP-glucose were 13.8±2.8 $\mu$M in thoracic aorta (filled squares), 6.67±1.8 $\mu$M in abdominal aorta (filled triangles), and 3.1±0.3 $\mu$M in carotid artery (filled diamonds), respectively. At the highest concentration tested, maximal relaxation was between 40%–50% in all three tissues.

ADP-glucose induced potent vasorelaxant effects in serotonin-precontracted rat abdominal aorta with an EC50 value of 3.26±0.12 $\mu$M and about 80% maximal relaxation (FIG. 6B). ADP-glucose induced relaxation of serotonin-induced constrictions in carotid arteries with an EC50 value of 20.5±6.3 µM and 40% maximal relaxation. Serotonin-precontracted thoracic aorta were unresponsive to ADP-glucose. ADP-glucose had no effect on untreated arterial tissue at resting force.

These results indicate that ADP-glucose induces vasorelaxation in rat arterial tissues. ADP-glucose-induced inhibition of contractile responses in rat arterial tissues occurred at concentrations close to the observed EC50 values for inhibition of contraction in guinea pig ileum and for mobilization of intracellular calcium determined in receptor transfected cells.

All journal article, reference and patent citations provided above, in parentheses or otherwise, are incorporated herein by reference in their entirety.

Although the invention has been described with reference to the examples provided above, it should be understood that various modifications can be made without departing from the spirit of the invention. Accordingly, the invention is limited only by the claims.

What is claimed is:

1. A method of identifying an ADP-glucose receptor agonist or antagonist, comprising:
   (a) contacting an ADP-glucose receptor polypeptide with at least one candidate compound in the presence of ADP-glucose under conditions wherein said receptor produces a G-protein coupled signal in response to ADP-glucose, wherein said ADP-glucose receptor polypeptide has the amino acid sequence designated SEQ ID NO:2;
   (b) determining the ability of said candidate compound to alter production of said G-protein coupled signal, wherein a candidate compound that alters production of said signal is identified as an ADP-glucose receptor agonist or antagonist.

2. The method of claim 1, wherein said G-protein coupled signal is increased intracellular calcium ion concentration.

3. The method of claim 1, wherein said receptor is contacted with 2 or more different candidate compounds.

4. The method of claim 1, wherein said receptor is contacted with a library of candidate compounds.

5. The method of claim 1, wherein said receptor is contacted with 100 or more different compounds separately.

6. A method of identifying an ADP-glucose receptor agonist, comprising:
   (a) contacting an ADP-glucose receptor polypeptide with at least one candidate compound under conditions that permit said receptor to produce a G-protein coupled signal in response to ADP-glucose, wherein said ADP-glucose receptor polypeptide has the amino acid sequence designated SEQ ID NO:2; and
   (b) determining the ability of said candidate compound to increase production of said G-protein coupled signal, wherein a candidate compound that increases production of said signal is thereby identified as an ADP-glucose receptor agonist.

7. The method of claim 6, wherein said G-protein coupled signal is increased intracellular calcium ion concentration.

8. The method of claim 6, wherein said receptor is contacted with 2 or more different candidate compounds.

9. The method of claim 6, wherein said candidate compound contacts said ADP-glucose receptor polypeptide in the presence of ADP-glucose.

10. The method of claim 6, wherein said receptor is contacted with a library of candidate compounds.

11. The method of claim 6, wherein said receptor is contacted with 100 or more different compounds separately.

12. A method of identifying an ADP-glucose receptor ligand, comprising:
   (a) contacting an ADP-glucose receptor polypeptide with at least one candidate compound under conditions that permit said receptor to selectively bind ADP-glucose, wherein said ADP-glucose receptor polypeptide has the amino acid sequence designated SEQ ID NO:2; and
   (b) determining the ability of said candidate compound to bind said ADP glucose receptor, wherein a candidate compound that selectively binds said ADP-glucose receptor is thereby identified as an ADP-glucose receptor ligand.

13. The method of claim 12, wherein said receptor is contacted with 2 or more different candidate compounds.

14. The method of claim 12, wherein said candidate compound contacts said ADP-glucose receptor polypeptide in the presence of ADP-glucose.

15. The method of claim 12, wherein said receptor is contacted with a library of candidate compounds.

16. The method of claim 12, wherein said receptor is contacted with 100 or more different compounds separately.

17. A method of identifying an ADP-glucose receptor ligand, comprising:
   (a) contacting an ADP-glucose receptor polypeptide with at least one candidate compound in the presence of ADP-glucose under conditions that permit said receptor to selectively bind ADP-glucose, wherein said ADP-glucose receptor polypeptide has the amino acid sequence designated SEQ ID NO:2; and
   (b) determining the ability of said candidate compound to bind said ADP-glucose receptor, wherein a candidate compound that selectively binds said ADP-glucose receptor is thereby identified as an ADP-glucose receptor ligand.

18. The method of claim 17, wherein maid receptor is contacted with 2 or more different candidate compounds.

19. The method of claim 17, wherein said receptor is contacted with a library of candidate compounds.

20. The method of claim 17, wherein said receptor is contacted with 100 or more different compounds separately.

* * * * *

UNITED STATES PATENT AND TRADEMARK OFFICE
CERTIFICATE OF CORRECTION

PATENT NO. : 6,790,608 B2
DATED : September 14, 2004
INVENTOR(S) : Civelli, Olivier et al.

Page 1 of 1

It is certified that error appears in the above-identified patent and that said Letters Patent is hereby corrected as shown below:

<u>Title page, Item [54] and Column 1, line 1,</u>
Title, please delete "AND" and replace therefore with -- AN --.

<u>Column 32,</u>
Line 48, please delete "maid" and replace therefore with -- said --.

Signed and Sealed this

Twenty-eighth Day of December, 2004

JON W. DUDAS
*Director of the United States Patent and Trademark Office*